US008314105B2

(12) United States Patent
Johnson

(10) Patent No.: US 8,314,105 B2
(45) **Date of Patent: *Nov. 20, 2012**

(54) METHODS OF REDUCING RISK OF INFECTION FROM PATHOGENS

(75) Inventor: Michael Ross Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 1474 days.

This patent is subject to a terminal disclaimer.

(21) Appl. No.: 11/835,902

(22) Filed: Aug. 8, 2007

(65) Prior Publication Data

US 2011/0144338 A1 Jun. 16, 2011

Related U.S. Application Data

(63) Continuation of application No. 10/920,484, filed on Aug. 18, 2004, now Pat. No. 7,745,442.

(60) Provisional application No. 60/496,482, filed on Aug. 20, 2003.

(51) Int. Cl.
*A61K 31/4965* (2006.01)
*C07D 241/02* (2006.01)

(52) U.S. Cl. ............... 514/255.01; 514/255.02; 544/407

(58) Field of Classification Search ............. 514/255.01, 514/255.02; 544/407
See application file for complete search history.

(56) References Cited

U.S. PATENT DOCUMENTS

| | | | |
|---|---|---|---|
| 3,313,813 | A | 4/1967 | Cragoe, Jr. |
| 3,316,266 | A | 4/1967 | Tull et al. |
| 3,325,494 | A | 6/1967 | Weinstock et al. |
| 3,341,540 | A | 9/1967 | Cragoe, Jr. et al. |
| 3,359,269 | A | 12/1967 | Cragoe, Jr. et al. |
| 3,360,517 | A | 12/1967 | Cragoe, Jr. et al. |
| 3,361,748 | A | 1/1968 | Cragoe, Jr. et al. |
| 3,461,123 | A | 8/1969 | Jones et al. |
| 3,472,848 | A | 10/1969 | Cragoe, Jr. et al. |
| 3,487,082 | A | 12/1969 | Cragoe, Jr. et al. |
| 3,491,094 | A | 1/1970 | Cragoe, Jr. et al. |
| 3,503,973 | A | 3/1970 | Cragoe, Jr. et al. |
| 3,506,662 | A | 4/1970 | Cragoe, Jr. et al. |
| 3,507,865 | A | 4/1970 | Jones et al. |
| 3,507,866 | A | 4/1970 | Jones et al. |
| 3,515,723 | A | 6/1970 | Cragoe, Jr. et al. |
| 3,527,758 | A | 9/1970 | Cragoe, Jr. et al. |
| 3,531,484 | A | 9/1970 | Bicking et al. |
| 3,544,571 | A | 12/1970 | Cragoe, Jr. et al. |
| 3,555,023 | A | 1/1971 | Cragoe, Jr. et al. |
| 3,555,024 | A | 1/1971 | Cragoe, Jr. et al. |
| 3,573,305 | A | 3/1971 | Cragoe, Jr. et al. |
| 3,573,306 | A | 3/1971 | Shepard et al. |
| 3,575,975 | A | 4/1971 | Cragoe, Jr. et al. |
| 3,577,418 | A | 5/1971 | Cragoe, Jr. et al. |
| 3,586,688 | A | 6/1971 | Cragoe, Jr. et al. |
| 3,625,950 | A | 12/1971 | Cragoe, Jr. et al. |
| 3,660,397 | A | 5/1972 | Jones et al. |
| 3,660,400 | A | 5/1972 | Cragoe, Jr. et al. |
| 3,668,241 | A | 6/1972 | Cragoe, Jr. et al. |
| 3,794,734 | A | 2/1974 | Cragoe, Jr. et al. |
| 3,864,401 | A | 2/1975 | Schultz et al. |
| 3,894,065 | A | 7/1975 | Cragoe, Jr. et al. |
| 3,914,253 | A | 10/1975 | Cragoe, Jr. et al. |
| 3,928,624 | A | 12/1975 | Cragoe, Jr. et al. |
| 3,929,872 | A | 12/1975 | Cragoe, Jr. et al. |
| 3,931,239 | A | 1/1976 | Cragoe, Jr. et al. |
| 3,935,313 | A | 1/1976 | Aron-Samuel et al. |
| 3,948,895 | A | 4/1976 | Donald |
| 3,953,476 | A | 4/1976 | Cragoe, Jr. et al. |
| 3,956,374 | A | 5/1976 | Shepard et al. |
| 3,958,004 | A | 5/1976 | Cragoe, Jr. et al. |
| 3,966,966 | A | 6/1976 | Cragoe, Jr. et al. |
| 3,974,212 | A | 8/1976 | Cragoe, Jr. et al. |
| 3,976,681 | A | 8/1976 | Cragoe, Jr. et al. |
| 3,976,686 | A | 8/1976 | Cragoe, Jr. et al. |
| 3,979,361 | A | 9/1976 | Schultz et al. |
| 3,984,465 | A | 10/1976 | Cragoe, Jr. et al. |
| 3,984,552 | A | 10/1976 | Cragoe, Jr. et al. |
| 3,987,091 | A | 10/1976 | Cragoe, Jr. et al. |
| 3,989,749 | A | 11/1976 | Cragoe, Jr. et al. |
| 3,991,087 | A | 11/1976 | Cragoe, Jr. et al. |
| 3,991,106 | A | 11/1976 | Cragoe, Jr. et al. |
| 4,003,927 | A | 1/1977 | Woltersdorf, Jr. et al. |
| 4,006,180 | A | 2/1977 | Cragoe, Jr. et al. |
| 4,012,524 | A | 3/1977 | Cragoe, Jr. et al. |
| 4,018,802 | A | 4/1977 | Cragoe, Jr. et al. |
| 4,020,177 | A | 4/1977 | Cragoe, Jr. et al. |
| 4,022,794 | A | 5/1977 | Smith et al. |
| 4,025,625 | A | 5/1977 | Rooney et al. |

(Continued)

FOREIGN PATENT DOCUMENTS

WO WO0128584 A1 4/2001

(Continued)

OTHER PUBLICATIONS

U.S. Appl. No. 10/920,527, filed Aug. 18, 2004, Hopkins.
U.S. Appl. No. 11/573,693, filed Feb. 14, 2007, Johnson.
U.S. Appl. No. 11/573,413, filed Feb. 8, 2007, Johnson.
U.S. Appl. No. 11/573,421, filed Feb. 8, 2007, Johnson.
U.S. Appl. No. 11/696,003, filed Apr. 3, 2007, Johnson.
U.S. Appl. No. 11/852,003, filed Sep. 7, 2007, Johnson, et al.
U.S. Appl. No. 11/851,803, filed Sep. 7, 2007, Johnson, et al.
U.S. Appl. No. 11/960,989, filed Dec. 20, 2007, Johnson, et al.
U.S. Appl. No. 11/950,674, filed Dec. 5, 2007, Johnson, et al.
U.S. Appl. No. 12/049,946, filed Mar. 17, 2008, Johnson, et al.
U.S. Appl. No. 12/049,968, filed Mar. 17, 2008, Johnson, et al.

(Continued)

*Primary Examiner* — Samira Jean-Louis
(74) *Attorney, Agent, or Firm* — Oblon, Spivak, McClelland, Maier & Neustadt, L.L.P.

(57) ABSTRACT

Prophylactic treatment methods are provided for protection of individuals and/or populations against infection from airborne pathogens. In particular, prophylactic treatment methods are provided comprising administering a sodium channel blocker or pharmaceutically acceptable salts thereof to one or more members of a population at risk of exposure to or already exposed to one or more airborne pathogens, either from natural sources or from intentional release of pathogens into the environment.

1 Claim, 10 Drawing Sheets

U.S. PATENT DOCUMENTS

| | | |
|---|---|---|
| 4,029,803 A | 6/1977 | Hunter et al. |
| 4,029,816 A | 6/1977 | Cragoe, Jr. et al. |
| 4,033,996 A | 7/1977 | Cragoe, Jr. et al. |
| 4,044,153 A | 8/1977 | Schultz et al. |
| 4,054,652 A | 10/1977 | Rooney et al. |
| 4,055,596 A | 10/1977 | Cragoe, Jr. et al. |
| 4,055,597 A | 10/1977 | Cragoe, Jr. et al. |
| 4,059,587 A | 11/1977 | Smith et al. |
| 4,059,601 A | 11/1977 | Cragoe, Jr. et al. |
| 4,059,602 A | 11/1977 | Cragoe, Jr. et al. |
| 4,061,643 A | 12/1977 | Cragoe, Jr. et al. |
| 4,066,675 A | 1/1978 | Cragoe, Jr. et al. |
| 4,066,692 A | 1/1978 | Cragoe, Jr. et al. |
| 4,067,980 A | 1/1978 | Cragoe, Jr. et al. |
| 4,070,464 A | 1/1978 | Cragoe, Jr. et al. |
| 4,070,539 A | 1/1978 | Cragoe, Jr. et al. |
| 4,081,554 A | 3/1978 | Cragoe, Jr. et al. |
| 4,085,117 A | 4/1978 | Cragoe, Jr. et al. |
| 4,085,125 A | 4/1978 | Cragoe, Jr. et al. |
| 4,085,211 A | 4/1978 | Cragoe, Jr. et al. |
| 4,085,219 A | 4/1978 | Cragoe, Jr. et al. |
| 4,087,435 A | 5/1978 | Cragoe, Jr. et al. |
| 4,087,526 A | 5/1978 | Cragoe, Jr. et al. |
| 4,087,542 A | 5/1978 | Cragoe, Jr. et al. |
| 4,091,105 A | 5/1978 | Rokach et al. |
| 4,091,107 A | 5/1978 | Cragoe, Jr. et al. |
| 4,092,356 A | 5/1978 | Cragoe, Jr. et al. |
| 4,092,414 A | 5/1978 | Cragoe, Jr. et al. |
| 4,096,267 A | 6/1978 | Cragoe, Jr. et al. |
| 4,097,504 A | 6/1978 | Cragoe, Jr. et al. |
| 4,100,294 A | 7/1978 | Cragoe, Jr. et al. |
| 4,102,888 A | 7/1978 | Smith et al. |
| 4,105,769 A | 8/1978 | Rooney et al. |
| 4,108,859 A | 8/1978 | Tong |
| 4,111,877 A | 9/1978 | Dixon et al. |
| 4,112,236 A | 9/1978 | Bicking et al. |
| 4,115,402 A | 9/1978 | Cragoe, Jr. et al. |
| 4,115,573 A | 9/1978 | Cragoe, Jr. et al. |
| 4,126,629 A | 11/1978 | Cragoe, Jr. et al. |
| 4,127,584 A | 11/1978 | Rokach et al. |
| 4,128,564 A | 12/1978 | Cragoe, Jr. et al. |
| 4,133,885 A | 1/1979 | Bolhofer et al. |
| 4,140,776 A | 2/1979 | Cragoe, Jr. et al. |
| 4,140,861 A | 2/1979 | Cragoe, Jr. et al. |
| 4,145,551 A | 3/1979 | Cragoe, Jr. et al. |
| 4,150,235 A | 4/1979 | Cragoe, Jr. et al. |
| 4,154,742 A | 5/1979 | Cragoe, Jr. et al. |
| 4,155,908 A | 5/1979 | Cragoe, Jr. et al. |
| 4,156,005 A | 5/1979 | Stokker et al. |
| 4,159,279 A | 6/1979 | Smith et al. |
| 4,163,781 A | 8/1979 | Cragoe, Jr. et al. |
| 4,163,794 A | 8/1979 | Cragoe, Jr. et al. |
| 4,166,177 A | 8/1979 | Cragoe, Jr. et al. |
| 4,175,203 A | 11/1979 | Cragoe, Jr. et al. |
| 4,177,285 A | 12/1979 | Cragoe, Jr. et al. |
| 4,178,386 A | 12/1979 | Williams et al. |
| 4,181,661 A | 1/1980 | Rooney et al. |
| 4,181,727 A | 1/1980 | Cragoe, Jr. et al. |
| 4,182,764 A | 1/1980 | Cragoe, Jr. et al. |
| 4,187,315 A | 2/1980 | Cragoe, Jr. et al. |
| 4,189,496 A | 2/1980 | Cragoe, Jr. et al. |
| 4,190,655 A | 2/1980 | DeMarco et al. |
| 4,196,292 A | 4/1980 | Woltersdorf, Jr. et al. |
| 4,203,988 A | 5/1980 | Bolhofer et al. |
| 4,207,329 A | 6/1980 | Williams et al. |
| 4,208,413 A | 6/1980 | Cragoe, Jr. et al. |
| 4,220,654 A | 9/1980 | Bolhofer et al. |
| 4,221,790 A | 9/1980 | Cragoe, Jr. et al. |
| 4,224,447 A | 9/1980 | Woltersdorf, Jr. et al. |
| 4,225,609 A | 9/1980 | Cragoe, Jr. et al. |
| 4,226,867 A | 10/1980 | Cragoe, Jr. et al. |
| 4,229,456 A | 10/1980 | Bolhofer et al. |
| 4,233,452 A | 11/1980 | Williams et al. |
| 4,237,130 A | 12/1980 | Cragoe, Jr. et al. |
| 4,237,144 A | 12/1980 | Cragoe, Jr. et al. |
| 4,246,406 A | 1/1981 | Cragoe, Jr. et al. |
| 4,249,021 A | 2/1981 | Cragoe, Jr. et al. |
| 4,256,758 A | 3/1981 | Cragoe, Jr. et al. |
| 4,260,771 A | 4/1981 | Cragoe, Jr. et al. |
| 4,263,207 A | 4/1981 | Rokach et al. |
| 4,267,341 A | 5/1981 | Rokach et al. |
| 4,272,537 A | 6/1981 | Woltersdorf, Jr. et al. |
| 4,277,602 A | 7/1981 | Woltersdorf et al. |
| 4,282,365 A | 8/1981 | Rokach et al. |
| 4,291,050 A | 9/1981 | Woltersdorf, Jr. et al. |
| 4,292,430 A | 9/1981 | Rokach et al. |
| 4,294,829 A | 10/1981 | Suzuki et al. |
| 4,296,122 A | 10/1981 | Cragoe, Jr. et al. |
| 4,296,237 A | 10/1981 | Cragoe, Jr. |
| 4,298,743 A | 11/1981 | Cragoe, Jr. et al. |
| 4,309,540 A | 1/1982 | Bock et al. |
| 4,316,043 A | 2/1982 | Cragoe, Jr. et al. |
| 4,317,822 A | 3/1982 | Woltersdorf, Jr. et al. |
| 4,317,922 A | 3/1982 | Cragoe, Jr. et al. |
| 4,336,397 A | 6/1982 | Cragoe, Jr. et al. |
| 4,337,258 A | 6/1982 | Rooney et al. |
| 4,337,354 A | 6/1982 | Cragoe, Jr. et al. |
| 4,342,776 A | 8/1982 | Cragoe, Jr. et al. |
| 4,342,782 A | 8/1982 | Cragoe, Jr. |
| 4,349,561 A | 9/1982 | Cragoe, Jr. et al. |
| 4,356,313 A | 10/1982 | Cragoe, Jr. et al. |
| 4,356,314 A | 10/1982 | Cragoe, Jr. et al. |
| 4,362,724 A | 12/1982 | Bock et al. |
| 4,375,475 A | 3/1983 | Willard et al. |
| 4,377,588 A | 3/1983 | Cragoe, Jr. et al. |
| 4,379,791 A | 4/1983 | Cragoe, Jr. et al. |
| 4,389,393 A | 6/1983 | Schor et al. |
| 4,389,417 A | 6/1983 | Bourke et al. |
| 4,390,537 A | 6/1983 | Cragoe, Jr. |
| 4,394,385 A | 7/1983 | Cragoe, Jr. |
| 4,394,515 A | 7/1983 | Rokach et al. |
| 4,401,669 A | 8/1983 | Cragoe, Jr. et al. |
| 4,420,615 A | 12/1983 | Bolhofer et al. |
| 4,425,337 A | 1/1984 | Alexander et al. |
| 4,428,956 A | 1/1984 | Cragoe, Jr. et al. |
| 4,428,959 A | 1/1984 | Cragoe, Jr. et al. |
| 4,431,652 A | 2/1984 | Cragoe, Jr. et al. |
| 4,431,660 A | 2/1984 | Cragoe, Jr. et al. |
| 4,432,992 A | 2/1984 | Cragoe, Jr. et al. |
| 4,440,740 A | 4/1984 | Fix et al. |
| 4,448,786 A | 5/1984 | Cragoe, Jr. et al. |
| 4,454,132 A | 6/1984 | Bock et al. |
| 4,459,422 A | 7/1984 | Willard et al. |
| 4,463,208 A | 7/1984 | Cragoe, Jr. et al. |
| 4,464,363 A | 8/1984 | Higuchi et al. |
| 4,465,850 A | 8/1984 | Cragoe, Jr. et al. |
| 4,501,729 A | 2/1985 | Boucher et al. |
| 4,510,322 A | 4/1985 | Blaine et al. |
| 4,536,507 A | 8/1985 | Rokach et al. |
| 4,537,902 A | 8/1985 | Cragoe, Jr. et al. |
| 4,567,289 A | 1/1986 | Willard et al. |
| 4,579,869 A | 4/1986 | Cragoe, Jr. et al. |
| 4,582,842 A | 4/1986 | Cragoe, Jr. et al. |
| 4,594,349 A | 6/1986 | Beyer et al. |
| 4,596,821 A | 6/1986 | Cragoe, Jr. et al. |
| 4,604,396 A | 8/1986 | Cragoe, Jr. et al. |
| 4,604,403 A | 8/1986 | Cragoe, Jr. et al. |
| 4,605,663 A | 8/1986 | Cragoe, Jr. et al. |
| 4,605,664 A | 8/1986 | Cragoe, Jr. et al. |
| 4,625,047 A | 11/1986 | Cragoe, Jr. et al. |
| 4,634,717 A | 1/1987 | Cragoe, Jr. et al. |
| 4,654,365 A | 3/1987 | Cragoe, Jr. et al. |
| 4,663,322 A | 5/1987 | Beyer et al. |
| 4,675,341 A | 6/1987 | Cragoe, Jr. |
| 4,680,414 A | 7/1987 | Cragoe, Jr. et al. |
| 4,699,917 A | 10/1987 | Cragoe, Jr. et al. |
| 4,699,926 A | 10/1987 | Abraham et al. |
| 4,710,513 A | 12/1987 | Willard et al. |
| 4,719,310 A | 1/1988 | Pietruszkiewicz et al. |
| 4,731,381 A | 3/1988 | Abraham et al. |
| 4,731,470 A | 3/1988 | Pietruszkiewicz et al. |
| 4,731,471 A | 3/1988 | Cragoe, Jr. et al. |
| 4,731,472 A | 3/1988 | Pietruszkiewicz et al. |
| 4,731,473 A | 3/1988 | Abraham et al. |
| 4,751,244 A | 6/1988 | Abraham et al. |
| 4,754,061 A | 6/1988 | Cragoe, Jr. et al. |
| 4,769,370 A | 9/1988 | Woltersdorf, Jr. et al. |

| | | |
|---|---|---|
| 4,771,076 A | 9/1988 | Cragoe, Jr. et al. |
| 4,775,695 A | 10/1988 | Cragoe, Jr. et al. |
| 4,777,281 A | 10/1988 | Woltersdorf, Jr. et al. |
| 4,778,897 A | 10/1988 | Cragoe, Jr. et al. |
| 4,782,073 A | 11/1988 | Cragoe, Jr. |
| 4,797,391 A | 1/1989 | Woltersdorf, Jr. et al. |
| 4,835,142 A | 5/1989 | Suzuki et al. |
| 4,835,313 A | 5/1989 | Pietruszkiewicz et al. |
| 4,894,376 A | 1/1990 | Morad et al. |
| 4,923,874 A | 5/1990 | McMahon et al. |
| 4,937,232 A | 6/1990 | Bell et al. |
| 4,952,582 A | 8/1990 | Beyer et al. |
| 5,132,296 A | 7/1992 | Cherksey |
| 5,215,991 A | 6/1993 | Burke |
| 5,242,947 A | 9/1993 | Cherksey et al. |
| 5,292,498 A | 3/1994 | Boucher, Jr. |
| 5,312,820 A | 5/1994 | Ashton et al. |
| 5,384,128 A | 1/1995 | Meezan et al. |
| 5,420,116 A | 5/1995 | Puchelle et al. |
| 5,449,682 A | 9/1995 | Greenlee et al. |
| 5,512,269 A | 4/1996 | Molina y Vedia et al. |
| 5,538,991 A | 7/1996 | Ashton et al. |
| 5,618,557 A | 4/1997 | Wille et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,683,675 A | 11/1997 | Molina y Vedia et al. |
| 5,707,644 A | 1/1998 | Illum |
| 5,716,931 A | 2/1998 | Molina y Vedia et al. |
| 5,725,842 A | 3/1998 | Boucher, Jr. et al. |
| 5,750,697 A | 5/1998 | Cherksey |
| 5,849,706 A | 12/1998 | Molina y Vedia et al. |
| 5,866,610 A | 2/1999 | Lang et al. |
| 5,902,567 A | 5/1999 | Boucher, Jr. |
| 5,908,611 A | 6/1999 | Gottlieb et al. |
| 5,935,555 A | 8/1999 | Stutts, III et al. |
| 5,955,100 A | 9/1999 | Bosslet et al. |
| 5,962,477 A | 10/1999 | Mak |
| 5,994,336 A | 11/1999 | Zasloff et al. |
| 6,015,828 A | 1/2000 | Cuppoletti et al. |
| 6,022,527 A | 2/2000 | Boucher, Jr. et al. |
| 6,033,688 A | 3/2000 | Mrsny et al. |
| 6,051,576 A | 4/2000 | Ashton et al. |
| 6,071,910 A | 6/2000 | Gleich et al. |
| 6,133,247 A | 10/2000 | Boucher, Jr. |
| 6,136,294 A | 10/2000 | Adjei et al. |
| 6,143,279 A | 11/2000 | Boucher, Jr. et al. |
| 6,153,187 A | 11/2000 | Yacoby-Zeevi |
| 6,159,968 A | 12/2000 | Cuppoletti |
| 6,190,691 B1 | 2/2001 | Mak |
| 6,204,270 B1 | 3/2001 | Ron et al. |
| 6,214,536 B1 | 4/2001 | Boucher, Jr. |
| 6,235,266 B1 | 5/2001 | Stutts, III et al. |
| 6,264,975 B1 | 7/2001 | Boucher, Jr. |
| 6,294,188 B1 | 9/2001 | Ragavan et al. |
| 6,297,226 B1 | 10/2001 | Glasky |
| 6,300,350 B1 | 10/2001 | Belloni et al. |
| 6,323,187 B1 | 11/2001 | Yerxa et al. |
| 6,344,475 B1 | 2/2002 | Caplan et al. |
| 6,399,585 B1 | 6/2002 | Larson et al. |
| 6,403,633 B2 | 6/2002 | Illig et al. |
| 6,451,288 B1 | 9/2002 | Boucher, Jr. et al. |
| 6,458,338 B1 | 10/2002 | Adjei et al. |
| 6,475,467 B1 | 11/2002 | Keller et al. |
| 6,476,048 B1 | 11/2002 | Szabo et al. |
| 6,858,614 B2 | 2/2005 | Johnson |
| 6,858,615 B2 | 2/2005 | Johnson |
| 6,903,105 B2 | 6/2005 | Johnson |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 7,317,013 B2 | 1/2008 | Johnson |
| 2003/0195160 A1 | 10/2003 | Johnson |
| 2003/0199456 A1 | 10/2003 | Johnson |
| 2004/0162296 A1 | 8/2004 | Johnson |
| 2004/0198744 A1 | 10/2004 | Johnson |
| 2004/0198745 A1 | 10/2004 | Johnson |
| 2004/0198746 A1 | 10/2004 | Johnson |
| 2004/0198747 A1 | 10/2004 | Johnson |
| 2004/0198748 A1 | 10/2004 | Johnson |
| 2004/0198749 A1 | 10/2004 | Johnson |
| 2004/0204424 A1 | 10/2004 | Johnson |
| 2004/0204425 A1 | 10/2004 | Johnson |
| 2004/0229884 A1 | 11/2004 | Johnson |
| 2005/0080092 A1 | 4/2005 | Johnson |
| 2005/0080093 A1 | 4/2005 | Johnson et al. |
| 2005/0090505 A1 | 4/2005 | Johnson et al. |
| 2005/0113388 A1 | 5/2005 | Johnson |
| 2005/0113389 A1 | 5/2005 | Johnson |
| 2005/0113390 A1 | 5/2005 | Johnson |
| 2005/0228182 A1 | 10/2005 | Johnson et al. |
| 2005/0234072 A1 | 10/2005 | Johnson et al. |
| 2006/0040954 A1 | 2/2006 | Johnson |
| 2006/0052394 A1 | 3/2006 | Johnson et al. |
| 2006/0052395 A1 | 3/2006 | Johnson et al. |
| 2006/0063780 A1 | 3/2006 | Johnson |
| 2006/0142306 A1 | 6/2006 | Johnson |
| 2006/0142581 A1 | 6/2006 | Johnson |
| 2006/0205738 A1 | 9/2006 | Johnson et al. |
| 2007/0032509 A1 | 2/2007 | Johnson et al. |
| 2007/0265280 A1 | 11/2007 | Johnson |

FOREIGN PATENT DOCUMENTS

| | | |
|---|---|---|
| WO | WO-03/070182 | 8/2003 |
| WO | WO-03/070184 | 8/2003 |
| WO | WO2004073629 A2 | 9/2004 |
| WO | WO2005016879 A2 | 2/2005 |
| WO | WO2005018644 A1 | 3/2005 |
| WO | WO2005025496 A2 | 3/2005 |

OTHER PUBLICATIONS

U.S. Appl. No. 12/049,894, filed Mar. 17, 2008, Johnson, et al.
U.S. Appl. No. 12/050,010, filed Mar. 17, 2008, Johnson.
U.S. Appl. No. 12/049,993, filed Mar. 17, 2008, Johnson.
U.S. Appl. No. 12/050,019, filed Mar. 17, 2008, Johnson.
U.S. Appl. No. 12/061,837, filed Apr. 3, 2008, Johnson, et al.
U.S. Appl. No. 12/061,864, filed Apr. 3, 2008, Johnson, et al.
U.S. Appl. No. 12/098,581, filed Apr. 7, 2008, Johnson.
Barrett, et al., Chloride Secretion by the Intestinal Epithelium: Molecular Basis Andregulatory Aspects, Annu. Rev. Physiol. (2000), 62: 535-572. (Abstract Only).
Bicking, et al., Pyrazine Diuretics. I. N-Amidino-3-amino-6-halopyrazinecarboxamides, J. Med. Chem, (1965) 8: 638-642.
Cocks, et al., British Journal of Pharmacology, (1988) 95: 67-76 (Abstract only).
Cohn et al., In vitro activity of amiloride combined with tobramycin against Pseudomonas isolates from patients with cystic fibrosis, Antimicrob Agents Chemother. Mar. 1988;32(3):395-6. PubMed ID: 3364958.
Cohn et al., In vitro antimicrobial activity of amiloride analogs against Pseudomonas, Chemotherapy (1992) 38(4):232-7. PubMed: 1473362.
Epand, et al., Reversal of Intrinsic Multidrug Resistance in Chinese Hamster Ovary Cells by Amiloride Analogs, Br. J. Cancer (1991) 63: 247-251 (Abstract Only).
Giunta et al., Amiloride, a diuretic with in vitro antimicrobial activity, Pharmacol Res Commun. Aug. 1984;16(8):821-9. PubMed 6494222.
Kleyman et al., American Journal of Physiology, (1991) 260: C271-C276 (Abstract Only).
Kleyman, et al., New Amiloride Analogs as Hapten to Raise Anti-Amiloride Antibodies, American Journal of Physiology, (1986) 250: C165-70 (Abstract Only).

Lammas, D. A.,et al., "ATP-Induced Killing of Mycobacteria by Human Macrophages is Mediated by Purinergic P2Z(P2X7) Receptors", Immunity, vol. 7, 433-444 (Sep. 1997).
Mastronarde, John G.,et al., "Amiloride inhibits cytokine production in epithelium infected with respiratory syncytial virus", American Journal of Physiology, 271(2, Pt. 1), pp. L201-L207 (1996).
Cragoe, Jr., Edward J.,et al.,"Chapter 7: Diuretic Agents",*Annual Reports in Medicinal Chemistry*, pp. 59-68 (1966).
Cragoe, Jr., Edward J.,et al.,"Chapter 7: Diuretic Agents",*Annual Reports in Medicinal Chemistry*, pp. 67-77 (1965).
Cragoe, Jr., Edward J.,"Structure-Activity Relationships in the Amiloride Series",*Merck Sharp and Dohme Research Laboratories*, pp. 1-20 (1979).
Cragoe, Jr., Edward J.,"The Synthesis of Amiloride and Its Analogs",pp. 24-38, Chapter 3.
Kleyman,Thomas R.,et al.,"Amiloride and Its Analogs as Tools in the Study of Ion Transport",*The Journal of Membrane Biology*, vol. 105, pp. 1-21 (1988).
Knowles, Michael R.,et al.,"Amiloride in Cystic Fibrosis: Safety, Pharmacokinetics, and Efficacy in the Treatment of Pulmonary Disease",Chapter 20, pp. 301-316.
Li, Jack H.,et al.,"Steroselective Blockage of Amphibian Epithelial Sodium Channels by Amiloride Analogs", *The Journal of Pharmacology and Experimental Therapeutics*, vol. 267, No. 3, pp. 1081-1084 (1993).
Sabater, J.R. ,et al.,"Aerosolization of P2y2-Receptor Agonists Enhances Mucociliary Clearance in Sheep",*The American Physiological Society*, pp. 2191-2196.
Shah, M.D., Pallav L.,"Chapter 7, Progress in the Treatment of Pulmonary Disease in Cystic Fibrosis",*Annual Reports in Medicinal Chemistry*, vol. 36, pp. 67-76 (2001).
Simchowitz, Louis ,et al.,"An Overview of the Structure Activity Relations in the Amiloride Series",Chapter 2, pp. 9-25.
Smith, Robert L.,et al.,"Chapter 7: Diuretics",*Annual Reports in Medicinal Chemistry*, vol. 13, pp. 61-70 (1978).
Smith, Robert L.,et al.,"Chapter 8: Diuretics",*Annual Reports in Medicinal Chemistry*, vol. 11, pp. 71-79 (1976).
Tarran, R. ,et al.,"The CF Salt Controversy: In Vivo Observations and Therapeutic Approaches",*Molecular Cell*, vol. 8, pp. 149-158 (Jul. 2001).
Taylor, Edward C.,et al .,"A Facile Route to "Open Chain" Analogues of DDATHF",*Heterocycles*, vol. 28, No. 2 (1989).
Windscheif, Paul-Michael ,et al.,"Substituted Dipyridylethenes and -ethynes and Key Pyridine Building Blocks",*Synthesis*, pp. 87-92 (Jan. 1994).
Worlitzsch, Dieter ,et al.,"Effects of Reduced Mucus Oxygen Concentration in Airway Pseudomonas Infections of Cystic Fibrosis Patients",*The Journal of Clinical Investigation*, vol. 109, No. 3, pp. 317-336 (Feb. 2002).
U.S. Appl. No. 12/393,252, filed Feb. 26, 2009, Johnson.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 60/909,818, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 60/013,387, filed Dec. 13, 2007, Johnson, et al.
U.S. Appl. No. 60/030,313, filed Feb. 21, 2008, Johnson.
U.S. Appl. No. 60/031,466, filed Feb. 26, 2008, Johnson.
U.S. Appl. No. 12/171,814, filed Jul. 11, 2008, Johnson. et al.
U.S. Appl. No. 12/171,867, filed Jul. 11, 2008, Johnson. et al.
U.S. Appl. No. 12/171,897, filed Jul. 11, 2008, Johnson. et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 12/939,579, filed Nov. 4, 2010, Johnson, et al.
U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.
U.S. Appl. No. 13/353,018, filed Jan. 18, 2012, Johnson.

Note: A decrease in % retention equals enhanced MCC

METHODS OF REDUCING RISK OF INFECTION FROM PATHOGENS

CROSS REFERENCE TO RELATED APPLICATIONS

This application claims the benefit of U.S. Provisional Application No. 60/496,482, filed Aug. 20, 2003, incorporated herein by reference in its entirety.

BACKGROUND

1. Field of the Invention

The present invention relates to the use of sodium channel blockers for prophylactic, post-exposure prophylactic, preventive or therapeutic treatment against diseases or conditions caused by pathogens, particularly pathogens which may be used in bioterrorism.

2. Description of the Related Art

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry. Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

BRIEF SUMMARY

The present invention provides such methods of prophylactic treatment. In one aspect, a prophylactic treatment method is provided comprising administering a prophylactically effective amount of a sodium channel blocker or a pharmaceutically acceptable salt thereof to an individual in need of prophylactic treatment against infection from one or more airborne pathogens.

In another aspect, a prophylactic treatment method is provided for reducing the risk of infection from an airborne pathogen which can cause a disease in a human, said method comprising administering an effective amount of a sodium channel blocker or a pharmaceutically acceptable salt thereof to the lungs of the human who may be at risk of infection from the airborne pathogen but is asymptomatic for the disease, wherein the effective amount of a sodium channel blocker or a pharmaceutically acceptable salt is sufficient to reduce the risk of infection in the human.

In another aspect, a post-exposure prophylactic treatment or therapeutic treatment method is provided for treating infection from an airborne pathogen comprising administering an effective amount of a sodium channel blocker or a pharmaceutically acceptable salt thereof to the lungs of an individual in need of such treatment against infection from an airborne pathogen.

The sodium channel blockers which may be used in the methods exemplified include sodium channel blockers corresponding to compounds according to Formulas I, II and III. Formula I is represented as:

$$\text{(I)}$$

where X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R_2)^2$;

$R^1$ is hydrogen or lower alkyl;

each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_nC(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or $$-(CH_2)_n\underset{O}{\overset{O}{\diagdown}}\!\!\diagup\!\!\underset{R^7}{\overset{R^7}{\diagup}}\!\!;$$

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

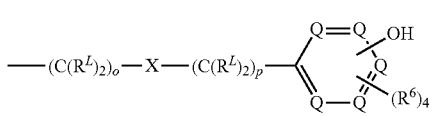 (A)

where each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

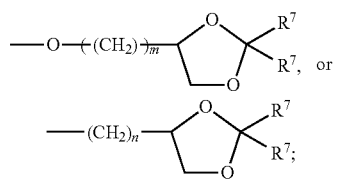

each o is, independently, an integer from 0 to 10;

each p is an integer from 0 to 10;

with the proviso that the sum of o and p in each contiguous chain is from 1 to 10;

each x is, independently, O, $NR^{10}$, $C(=O)$, CHOH, $C(=N-R^{10})$, $CHNR^7R^{10}$, or represents a single bond;

each $R^6$ is, independently, $-R^7$, $-OH$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_mR^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

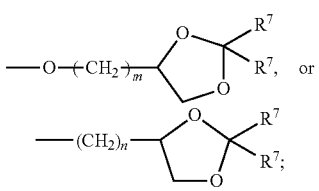

where when two $R^6$ are $-OR^{11}$ and are located adjacent to each other on a phenyl ring, the alkyl moieties of the two $R^6$ may be bonded together to form a methylenedioxy group;

each $R^7$ is, independently, hydrogen or lower alkyl;

each $R^8$ is, independently, hydrogen, lower alkyl, $-C(=O)-R^{11}$, glucuronide, 2-tetrahydropyranyl, or

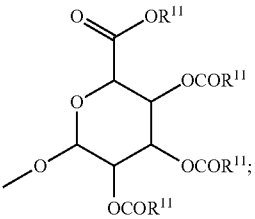

each $R^9$ is, independently, $-CO_2R^7$, $-CON(R^7)_2$, $-SO_2CH_3$, or $-C(=O)R^7$;

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, CHOH, $C(=O)$, $CHNR^7R^{10}$, $C=NR^{10}$, or $NR^{10}$;

each $R^{11}$ is, independently, lower alkyl;

each g is, independently, an integer from 1 to 6;

each m is, independently, an integer from 1 to 7;

each n is, independently, an integer from 0 to 7;

each Q is, independently, $C-R^6$ or a nitrogen atom, wherein at most three Q in a ring are nitrogen atoms;

or a pharmaceutically acceptable salt thereof, and inclusive of all enantiomers, diastereomers, and racemic mixtures thereof.

Formula II is represented as:

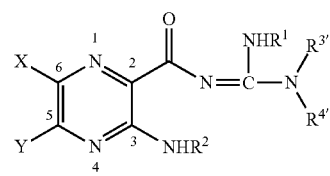 (II)

where X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$;

$R^1$ is hydrogen or lower alkyl;

each $R^2$ is, independently, $-R^7$, $-(CH_2)_m-OR^B$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m NR^{10}-CH_2(CHOR^8)(CHOR^8)_n-CH_2OR^8$, $-(CH_2)_n-CO_2R^7$, or

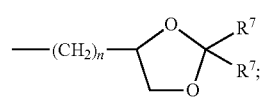

where when two $-CH_2OR^8$ groups are located 1,2- or 1,3- with respect to each other the $R^8$ groups may be joined to form a cyclic mono- or di-substituted 1,3-dioxane or 1,3-dioxolane;

$R^{3'}$ and $R^{4'}$ are each, independently, hydrogen, a group represented by formula (A'), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^{3'}$ and $R^{4'}$ is a group represented by formula (A'):

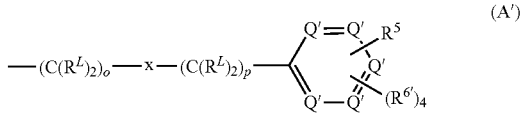
(A')

where each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_n-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

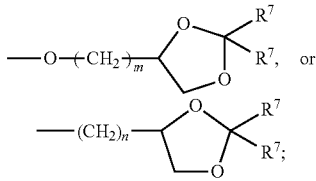

where when two $-CH_2OR^8$ groups are located 1,2- or 1,3- with respect to each other the $R^8$ groups may be joined to form a cyclic mono- or di-substituted 1,3-dioxane or 1,3-dioxolane;

each o is, independently, an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N-R^{10})$, $CHNR^7R^{10}$, or represents a single bond;
each $R^5$ is, independently, $-(CH_2)_n-NR^{12}R^{12}$, $-O-(CH_2)_m-NR^{11}R^{12}$, $-O-(CH_2)_n-NR^{12}R^{12}$, $-O-(CH_2)_m-(Z)_gR^{12}$, $-(CH_2)_nNR^{11}R^{11}$, $-O-(CH_2)_m NR^{11}R^{11}$, $-(CH_2)_n-N^{\oplus}-(R^{11})_3$, $-O-(CH_2)_m-N^{\oplus}-(R^{11})_3$, $-(CH_2)_n-(Z)_g-(CH_2)_m-NR^{10}R^{10}$, $-O-(CH_2)_m-(Z)_g-(CH_2)_m-NR^{10}R^{10}$, $-(CH_2CH_2O)_m-CH_2CH_2NR^{12}R^{12}$, $-O-(CH_2CH_2O)_m-CH_2CH_2NR^{12}R^{12}$, $-(CH_2)_n-C(=O)NR^{12}R^{12}$, $-O-(CH_2)_m-C(=O)NR^{12}R^{12}$, $-O-(CH_2)_m-(CHOR^8)_m CH_2NR^{10}-(Z)_g-R^{10}$, $-(CH_2)_n-(CHOR^8)_m CH_2-NR^{10}-(Z)_g-R^{10}$, $-(CH_2)_nNR^{10}-O(CH_2)_m(CHOR^8)_n CH_2NR^{10}-(Z)_g-R^{10}$, $-O(CH_2)_m-NR^{10}-(CH_2)_m-(CHOR^8)_nCH_2NR^{10}-(Z)_g-R^{10}$, -(Het)-$(CH_2)_m-OR^8$, -(Het)-$(CH_2)_m-NR^7R^{10}$, -(Het)-$(CH_2)_m(CHOR^8)(CHOR^8)_n-CH_2OR^8$, -(Het)-$(CH_2CH_2O)_m-R^8$, -(Het)-$(CH_2CH_2O)_m-CH_2CH_2NR^7R^{10}$, -(Het)-$(CH_2)_m-C(=O)NR^7R^{10}$, -(Het)-$(CH_2)_m-(Z)_g-R^7$, -(Het)-$(CH_2)_m-NR^{10}-CH_2(CHOR^8)(CHOR^8)_n-CH_2OR^8$, -(Het)-$(CH_2)_m-CO_2R^7$, -(Het)-$(CH_2)_m-NR^{12}R^{12}$, -(Het)-$(CH_2)_n-NR^{12}R^{12}$, -(Het)-$(CH_2)_m-(Z)_gR^{12}$, -(Het)-$(CH_2)_mNR^{11}R^{11}$, -(Het)-$(CH_2)_m-N^{\oplus}-(R^{11})_3$, -(Het)-$(CH_2)_m-(Z)_g-(CH_2)_m-NR^{10}R^{10}$, -(Het)-$(CH_2CH_2O)_m-CH_2CH_2NR^{12}R^{12}$, -(Het)-$(CH_2)_m-C(=O)NR^{12}R^{12}$, -(Het)-$(CH_2)_m-(CHOR^8)_mCH_2NR^{10}-(Z)_g-R^{10}$, -(Het)-$(CH_2)_m-NR^{10}-(CH_2)_m-(CHOR^8)_nCH_2NR^{10}-(Z)_g-R^{10}$, where when two $-CH_2OR^8$ groups are located 1,2- or 1,3- with respect to each other the $R^8$ groups may be joined to form a cyclic mono- or di-substituted 1,3-dioxane or 1,3-dioxolane, $-(CH_2)_n(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane, $-O-(CH_2)_m(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane, $-(CH_2)_n-NR^{10}-CH_2(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane, or $-O-(CH_2)_m-NR^{10}-CH_2(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane;

each $R^{6'}$ is, independently, $-R^5$, $-R^7$, $-OR^8$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

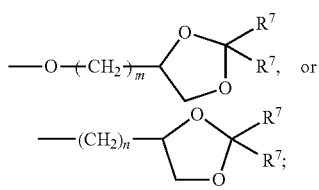

where when two $R^{6'}$ are $-OR^{11}$ and are located adjacent to each other on a phenyl ring, the alkyl moieties of the two $R^{6'}$ may be bonded together to form a methylenedioxy group and where when two $-CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen or lower alkyl;

each $R^8$ is, independently, hydrogen, lower alkyl, —C(=O)—$R^{11}$, glucuronide, 2-tetrahydropyranyl, or

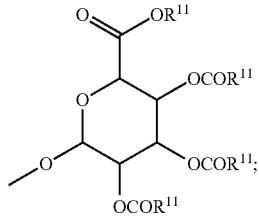

each $R^9$ is, independently, —$CO_2R^7$, —$CON(R^7)_2$, —$SO_2CH_3$, or —C(=O)$R^7$;

each $R^{10}$ is, independently, —H, —$SO_2CH_3$, —$CO_2R^7$, —C(=O)$NR^7R^9$, —C(=O)$R^7$, or —$CH_2$—$(CHOH)_n$—$CH_2OH$;

each Z is, independently, CHOH, C(=O), $CHNR^7R^{10}$, C=$NR^{10}$, or $NR^{10}$;

each $R^{11}$ is, independently, lower alkyl;

each $R^{12}$ is independently, —$SO_2CH_3$, —$CO_2R^7$, —C(=O)$NR^7R^9$, —C(=O)$R^7$, or —$CH_2$—$(CHOH)_n$—$CH_2OH$;

each Het is independently, —$NR^7$, —$NR^{10}$, —S—, —SO—, or —$SO_2$—;

each g is, independently, an integer from 1 to 6;

each m is, independently, an integer from 1 to 7;

each n is, independently, an integer from 0 to 7;

each Q' is, independently, C—$R^5$, C—$R^{6'}$, or a nitrogen atom, wherein at most three Q' in a ring are nitrogen atoms; or a pharmaceutically acceptable salt thereof, and inclusive of all enantiomers, diastereomers, and racemic mixtures thereof.

Formula III is represented as:

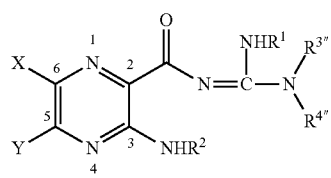

(III)

where X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or —$N(R^2)_2$;

$R^1$ is hydrogen or lower alkyl;

each $R^2$ is, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—C(=O)$NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

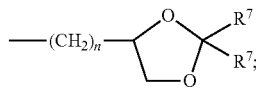

$R^{3''}$ and $R^{4''}$ are each, independently, hydrogen, a group represented by formula (A"), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^{3''}$ and $R^{4''}$ is a group represented by formula (A"):

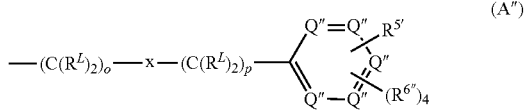

(A")

where each $R^L$ is, independently, —$R^7$, —$(CH_2)_n$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)$—$CO_2R^7$, —O—$(CH_2)_m$—$CO_2R^7$, —$OSO_3H$, —O-glucuronide, —O-glucose,

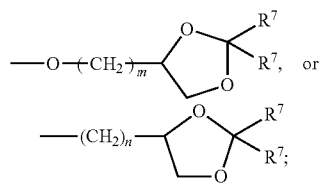

each o is, independently, an integer from 0 to 10;

each p is an integer from 0 to 10;

with the proviso that the sum of o and p in each contiguous chain is from 1 to 10;

each x is, independently, O, $NR^{10}$, C(=O), CHOH, C(=N—$R^{10}$), $CHNR^7R^{10}$, or represents a single bond;

each $R^{5'}$ is, independently, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—

$CH_2OR^8$, $-(CH_2)_n-CO_2R^7$, $-O-(CH_2)_m-CO_2R^7$, $-OSO_3H$, $-O$-glucuronide, $-O$-glucose,

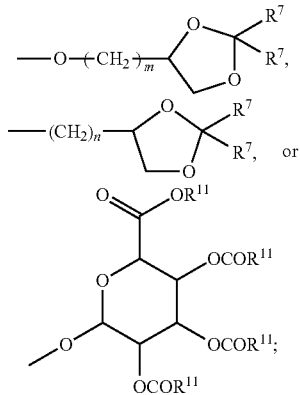

each $R^{6''}$ is, independently, $-R^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

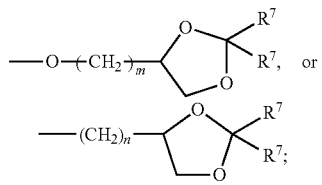

where when two $R^{6''}$ are $-OR^{11}$ and are located adjacent to each other on a phenyl ring, the alkyl moieties of the two $R^{6''}$ may be bonded together to form a methylenedioxy group;

each $R^7$ is, independently, hydrogen or lower alkyl;

each $R^8$ is, independently, hydrogen, lower alkyl, $-C(=O)-R^{11}$, glucuronide, 2-tetrahydropyranyl, or

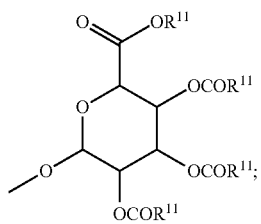

each $R^9$ is, independently, $-CO_2R^7$, $-CON(R^7)_2$, $-SO_2CH_3$, or $-C(=O)R^7$;

each $R^{10}$ is, independently, $-H$, $-SO_2CH_3$, $-CO_2R^7$, $-C(=O)NR^7R^9$, $-C(=O)R^7$, or $-CH_2-(CHOH)-CH_2OH$;

each Z is, independently, CHOH, C(=O), $CHNR^7R^{10}$, $C=NR^{10}$, or $NR^{10}$;

each $R^{11}$ is, independently, lower alkyl;

each g is, independently, an integer from 1 to 6;

each m is, independently, an integer from 1 to 7;

each n is, independently, an integer from 0 to 7;

each Q" is, independently, $C-R^{5'}$, $C-R^{6''}$, or a nitrogen atom, wherein at most three Q" in a ring are nitrogen atoms; or a pharmaceutically acceptable salt thereof, and inclusive of all enantiomers, diastereomers, and racemic mixtures thereof.

BRIEF DESCRIPTION OF THE DRAWINGS

A more complete appreciation of the invention and many of the attendant advantages thereof will be readily obtained as the same becomes better understood by reference to the following detailed description considered in conjunction with the following figures.

DETAILED DESCRIPTION OF THE PREFERRED EMBODIMENTS

Figure 1:
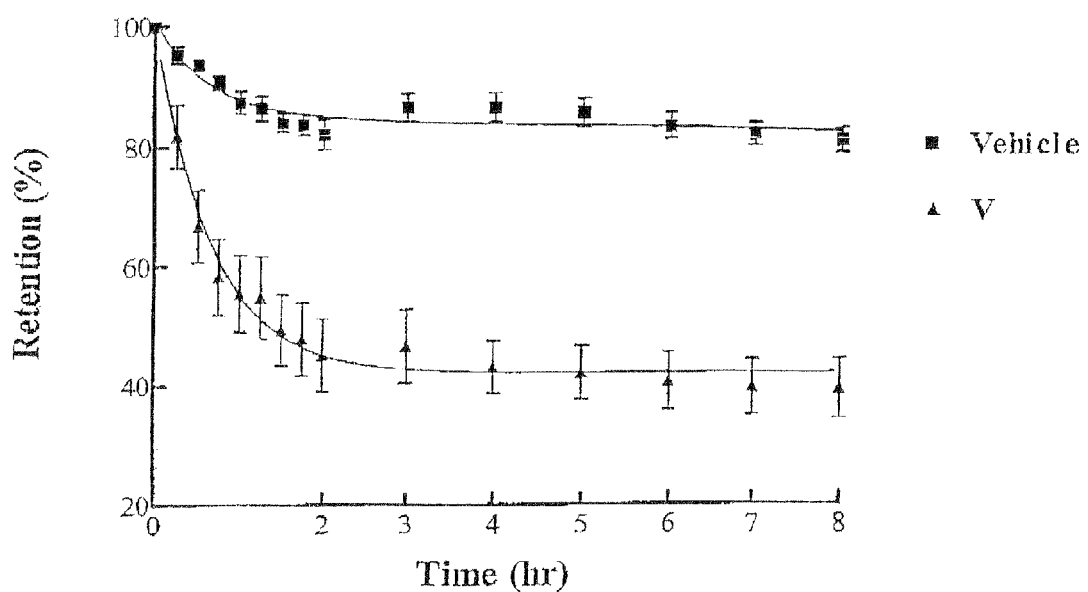
FIG. 1: Effect of a compound of Formula I on MCC at t=0 hrs as described in the Examples herein.

The prophylactic or therapeutic treatment methods of the present invention may be used in situations where a segment of the population has been, or is believed to have been, exposed to one or more airborne pathogens. The prophylactic or therapeutic treatment methods may additionally be used in situations of ongoing risk of exposure to or infection from airborne pathogens. Such situations may arise due to naturally occurring pathogens or may arise due to a bioterrorism event wherein a segment of the population is intentionally exposed to one or more pathogens. The individuals or portion of the population believed to be at risk from infection can be treated according to the methods disclosed herein. Such treatment preferably will commence at the earliest possible time, either prior to exposure if imminent exposure to a pathogen is anticipated or possible or after the actual or suspected exposure. Typically, the prophylactic treatment methods will be used on humans asymptomatic for the disease for which the human is believed to be at risk. The term "asymptomatic" as used herein means not exhibiting medically recognized symptoms of the disease, not yet suffering from infection or disease from exposure to the airborne pathogens, or not yet testing positive for a disease. The treatment methods may involve post-exposure prophylactic or therapeutic treatment, as needed.

Many of the pathogenic agents identified by NIAID have been or are capable of being aerosolized such that they may enter the body through the mouth or nose, moving into the bodily airways and lungs. These areas of the body have mucosal surfaces which naturally serve, in part, to defend against foreign agents entering the body. The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water and a cation counter-ion, and epithelial liquid absorption, often reflecting $Na^+$ absorption, coupled with water and counter anion ($Cl^-$ and/or $HCO_3^-$).

R. C. Boucher, in U.S. Pat. No. 6,264,975, describes methods of hydrating mucosal surfaces, particularly nasal airway surfaces, by administration of pyrazinoylguanidine sodium channel blockers. These compounds, typified by amiloride, benzamil and phenamil, are effective for hydration of the mucosal surfaces. U.S. Pat. No. 5,656,256, describes methods of hydrating mucous secretions in the lungs by administration of benzamil or phenamil, for example, to treat diseases such as cystic fibrosis and chronic bronchitis. U.S. Pat. No. 5,725,842 is directed to methods of removing retained mucus secretions from the lungs by administration of amiloride.

It has now been discovered that certain sodium channel blockers described and exemplified in U.S. patent application Ser. Nos. 10/076,551, filed Feb. 19, 2002, (U.S. Patent Application Publication No. 2003/0195160, 10/367,947, filed Feb. 19, 2003, and 10/076,571, filed Feb. 19, 2002, (U.S. Patent Application Publication No. 2003/0199456, and PCT publications WO 03/070184, published Aug. 28, 2003, and WO 03/070182, published Aug. 28, 2003, incorporated herein in their entirety by reference, may be used in prophylactic treatment methods to protect humans in whole or in part, against the risk of infection from pathogens which may or may not have been purposely introduced into the environment, typically into the air, of a populated area. Such treatment may be effectively used to protect those who may have been exposed where a vaccine is not available or has not been provided to the population exposed and/or in situations where treatments for the infection resulting from the pathogen to which a population has been subjected are insufficient or unavailable altogether.

Without being bound by any theory, it is believed that the sodium channel blockers disclosed herein surprisingly may be used on substantially normal or healthy lung tissue to prevent or reduce the uptake of airborne pathogens and/or to clear the lungs of all or at least a portion of such pathogens. Preferably, the sodium channel blockers will prevent or reduce the viral or bacterial uptake of airborne pathogens. The ability of sodium channel blockers to hydrate mucosal surfaces is believed to function to first hydrate lung mucous secretions, including mucous containing the airborne pathogens to which the human has been subjected, and then facilitate the removal of the lung mucous secretions from the body. By functioning to remove the lung mucous secretions from the body, the sodium channel blocker thus prevents or, at least, reduces the risk of infection from the pathogen(s) inhaled or brought into the body through a bodily airway.

The present invention is concerned primarily with the prophylactic, post exposure, rescue and therapeutic treatment of human subjects, but may also be employed for the treatment of other mammalian subjects, such as dogs and cats, for veterinary purposes, and to the extent the mammals are at risk of infection or disease from airborne pathogens.

The term "airway" as used herein refers to all airways in the respiratory system such as those accessible from the mouth or nose, including below the larynx and in the lungs, as well as air passages in the head, including the sinuses, in the region above the larynx.

The terms "pathogen" and "pathogenic agent" are interchangeable and, as used herein, mean any agent that can cause disease or a toxic substance produced by a pathogen that causes disease. Typically, the pathogenic agent will be a living organism that can cause disease. By way of example, a pathogen may be any microorganism such as bacterium, protozoan or virus that can cause disease.

The term "airborne pathogen" means any pathogen which is capable of being transmitted through the air and includes pathogens which travel through air by way of a carrier material and pathogens either artificially aerosolized or naturally occurring in the air.

The term "prophylactic" as used herein means the prevention of infection, the delay of infection, the inhibition of infection and/or the reduction of the risk of infection from pathogens and includes pre- and post-exposure to pathogens. The prophylactic effect may, inter alia, involve a reduction in the ability of pathogens to enter the body, or may involve the removal of all or a portion of pathogens which reach airways and airway surfaces in the body from the body prior to the pathogens initiating or causing infection or disease. The airways from which pathogens may be removed, in whole or part, include all bodily airways and airway surfaces with mucosal surfaces, including airway surfaces in the lungs.

The term "therapeutic" as used herein means to alleviate disease or infection from pathogens.

The compounds useful in this invention include sodium channel blockers such as those represented by Formulas I, II and III. The sodium channel blockers may be prepared by the procedures described in U.S. patent application Ser. Nos. 10/076,551, filed Feb. 19, 2002, (U.S. Patent Application Publication No. 2003/0195160), 10/367,947, filed Feb. 19, 2003, and 10/076,571, filed Feb. 19, 2002, (U.S. Patent Application Publication No. 2003/0199456), and PCT publications WO 03/070184, published Aug. 28, 2003, and WO 03/070182, published Aug. 28, 2003, incorporated herein in their entirety by reference, in combination with procedures known to those skilled in the art.

Formulas I, II and III may be represented as shown above. In the compounds represented by these formulas, examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

As to Formula I, in a preferred embodiment of Formula I, Y is $-NH_2$.

In another preferred embodiment of Formula I, $R^2$ is hydrogen.

In another preferred embodiment of Formula I, $R^1$ is hydrogen.

In another preferred embodiment of Formula I, X is chlorine.

In another preferred embodiment of Formula I, $R^3$ is hydrogen.

In another preferred embodiment of Formula I, $R^L$ is hydrogen.

In another preferred embodiment of Formula I, o is 4.

In another preferred embodiment of Formula I, p is 0.

In another preferred embodiment of Formula I, the sum of o and p is 4.

In another preferred embodiment of Formula I, x represents a single bond.

In another preferred embodiment of Formula I, $R^6$ is hydrogen.

In another preferred embodiment of Formula I, at most one Q is a nitrogen atom.

In another preferred embodiment of Formula I, no Q is a nitrogen atom.

In a preferred embodiment of Formula I:
X is halogen;
Y is $-N(R^7)_2$;
$R^1$ is hydrogen or $C_1$-$C_3$ alkyl;
$R^2$ is $-R^7$, $-OR^7$, $CH_2OR^7$, or $-CO_2R^7$;
$R^3$ is a group represented by formula (A); and
$R^4$ is hydrogen, a group represented by formula (A), or lower alkyl.

In another preferred embodiment of Formula I:
X is chloro or bromo;
Y is $-N(R^7)_2$;
$R^2$ is hydrogen or $C_1$-$C_3$ alkyl;
at most three $R^6$ are other than hydrogen as described above;
at most three $R^L$ are other than hydrogen as described above; and
at most 2 Q are nitrogen atoms.

In another preferred embodiment of Formula I: Y is $-NH_2$.

In another preferred embodiment of Formula I: $R^4$ is hydrogen;
at most one $R^L$ is other than hydrogen as described above;
at most two $R^6$ are other than hydrogen as described above; and
at most 1 Q is a nitrogen atom.

In another preferred embodiment, the compound of formula (I) is represented by the formula:

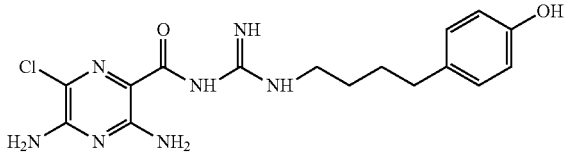

In another preferred embodiment, the compound of formula (I) is represented by the formula:

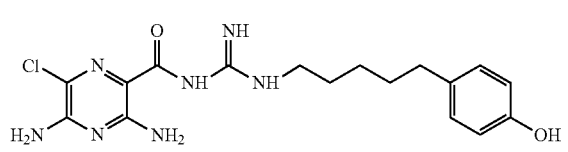

In another preferred embodiment, the compound of formula (I) is represented by the formula:

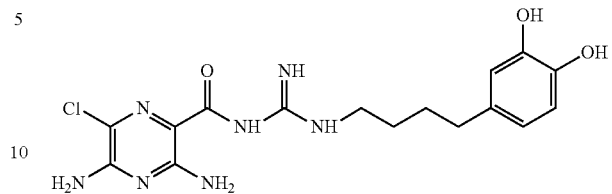

In another preferred embodiment, the compound of formula (I) is represented by the formula:

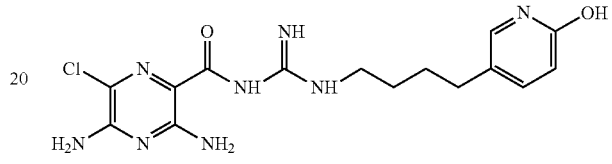

In another preferred embodiment, the compound of formula (I) is represented by the formula:

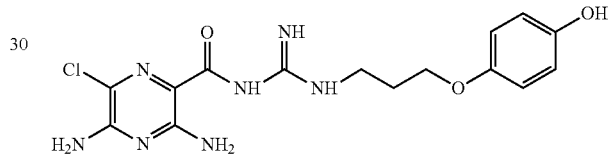

In another preferred embodiment, the compound of formula (I) is represented by the formula:

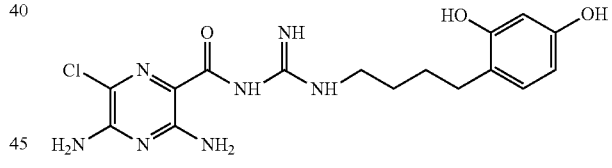

The sodium channel blocker may also be a compound of Formula II, shown above.

Hydrogen and lower alkyl, particularly $C_1$-$C_3$ alkyl are preferred for $R^2$ in Formula II. Hydrogen is particularly preferred.

For Formula II, $R^{3'}$ and $R^{4'}$ may be, independently, hydrogen, a group represented by formula (A'), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^{3'}$ and $R^{4'}$ is a group represented by formula (A').

Preferred compounds of Formula II are those where one of $R^{3'}$ and $R^{4'}$ is hydrogen and the other is represented by formula (A').

In formula (A'), the moiety $-(C(R^L)_2)_o$-x-$(C(R^L)_2)_p-$ defines an alkylene group bonded to the aromatic ring. The variables o and p may each be an integer from 0 to 10, subject to the proviso that the sum of o and p in the chain is from 0 to 10. Thus, o and p may each be 0, 1, 2, 3, 4, 5, 6, 7, 8, 9, or 10.

Preferably, the sum of o and p is from 2 to 6. In a particularly preferred embodiment of Formula II, the sum of o and p is 4.

The preferred $R^L$ groups for Formula II include —H, —OH, —N($R^7$)$_2$, especially where each $R^7$ is hydrogen.

In the alkylene chain in formula (A'), it is preferred that when one $R^L$ group bonded to a carbon atoms is other than hydrogen, then the other $R^L$ bonded to that carbon atom is hydrogen, i.e., the formula —CHR$^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of Formula II, all of the $R^L$ groups in the alkylene chain are hydrogen. In these embodiments, the alkylene chain is represented by the formula —(CH$_2$)$_o$-x-(CH$_2$)—.

Preferred examples of $R^5$ for Formula II include:
—N(SO$_2$CH$_3$)$_2$,
—CH$_2$—CHNHBocCO$_2$CH$_3$($\alpha$),
—O—CH$_2$—CHNH$_2$CO$_2$H($\alpha$),
—O—CH$_2$—CHNH$_2$CO$_2$CH$_3$($\alpha$),
—O—(CH$_2$)$_2$—N$^+$(CH$_3$)$_3$,
—C(=O)NH—(CH$_2$)$_2$—NH$_2$,
—C(=O)NH—(CH$_2$)$_2$—NH—C(=NH)—NH$_2$, and

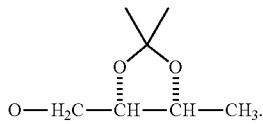

More specific examples of suitable groups represented by formula (A') are shown in formulas (B)-(E) below:

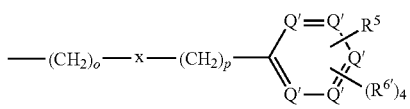 (B)

where o, x, p, $R^5$, and $R^6$, are as defined above;

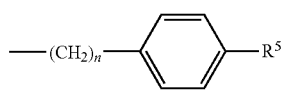 (C)

where n is an integer from 1 to 10 and $R^5$ is as defined above;

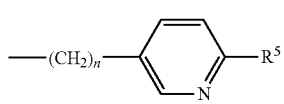 (D)

where n is an integer from 1 from 10 and $R^5$ is as defined above;

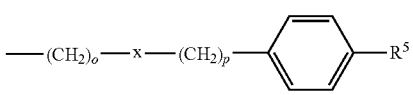 (E)

where o, x, p, and $R^5$ are as defined above.

In a preferred embodiment of Formula II, Y is —NH$_2$.

In another preferred embodiment of Formula II, $R^2$ is hydrogen.

In another preferred embodiment of Formula II, $R^1$ is hydrogen.

In another preferred embodiment of Formula II, X is chlorine.

In another preferred embodiment of Formula II, $R^3$ is hydrogen.

In another preferred embodiment of Formula II t, $R^L$ is hydrogen.

In another preferred embodiment of Formula II, o is 4.

In another preferred embodiment of Formula II, p is 0.

In another preferred embodiment of Formula II, the sum of o and p is 4.

In another preferred embodiment of Formula II, x represents a single bond.

In another preferred embodiment of Formula II, $R^{6'}$ is hydrogen.

In another preferred embodiment of Formula II, at most one Q' is a nitrogen atom.

In another preferred embodiment of Formula II, no Q' is a nitrogen atom.

In a preferred embodiment of Formula II:
X is halogen;
Y is —N($R^7$)$_2$;
$R^1$ is hydrogen or $C_1$-$C_3$ alkyl;
$R^2$ is —$R^7$, —O$R^7$, CH$_2$O$R^7$, or —CO$_2$$R^7$;
$R^{3'}$ is a group represented by formula (A'); and
$R^{4'}$ is hydrogen, a group represented by formula (A'), or lower alkyl.

In another preferred embodiment of Formula II:
X is chloro or bromo;
Y is —N($R^7$)$_2$;
$R^2$ is hydrogen or $C_1$-$C_3$ alkyl;
at most three $R^{6'}$ are other than hydrogen as described above;
at most three $R^L$ are other than hydrogen as described above; and
at most 2 Q' are nitrogen atoms.

In another preferred embodiment of Formula II:
Y is —NH$_2$.

In another preferred embodiment of Formula II:
$R^{4'}$ is hydrogen;
at most one $R^L$ is other than hydrogen as described above;
at most two $R^{6'}$ are other than hydrogen as described above; and
at most 1 Q' is a nitrogen atom.

Preferred examples of $R^5$ in the embodiments of Formula II described above include:
—N(SO$_2$CH$_3$)$_2$,
—CH$_2$—CHNHBocCO$_2$CH$_3$($\alpha$),
—O—CH$_2$—CHNH$_2$CO$_2$H($\alpha$),
—O—CH$_2$—CHNH$_2$CO$_2$CH$_3$($\alpha$),
—O—(CH$_2$)$_2$—N$^+$(CH$_3$)$_3$,
—C(=O)NH—(CH$_2$)$_2$—NH$_2$, and
—C(=O)NH—(CH$_2$)$_2$—NH—C(=NH)—NH$_2$.

Examples of compounds of Formula II include the following:

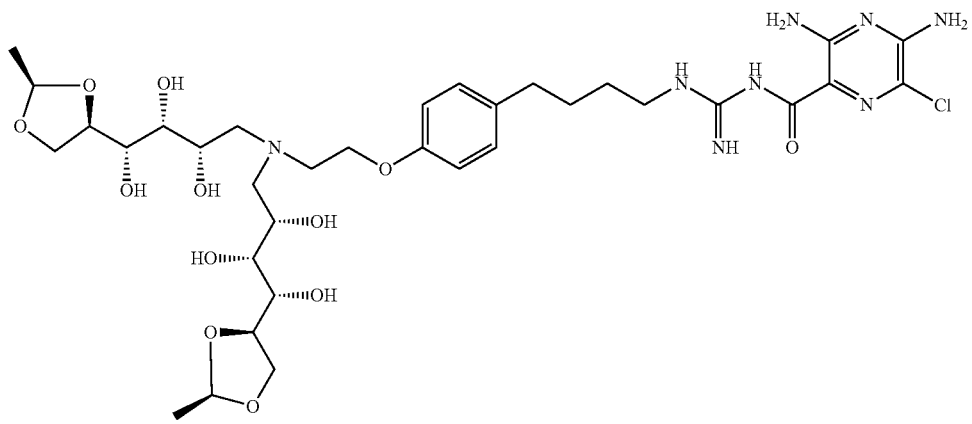
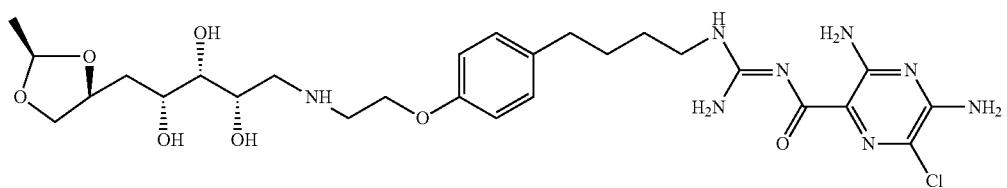
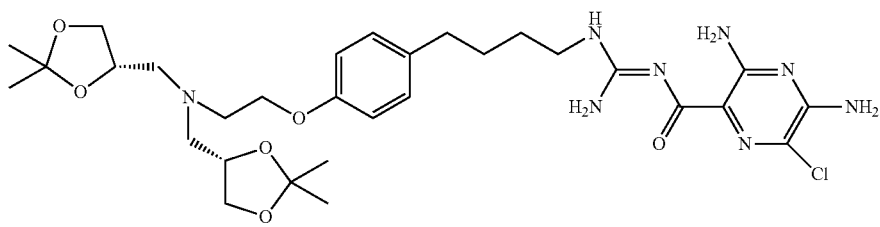
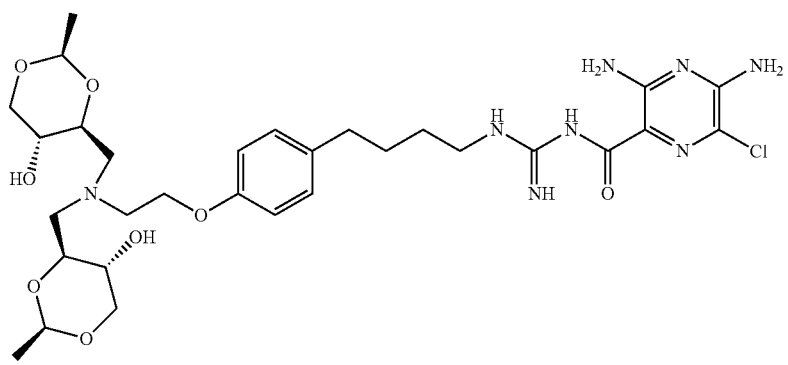
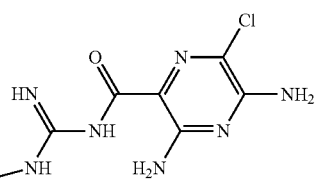
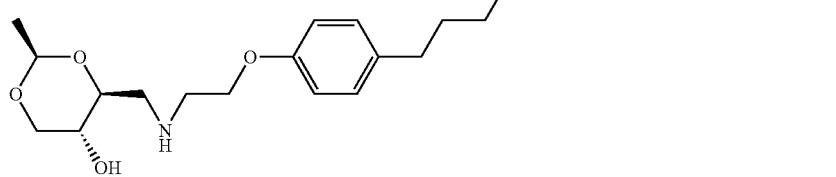

-continued

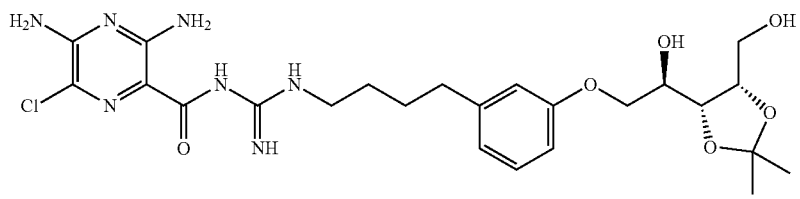

Formula III also represents sodium channel blockers which may be used in the methods exemplified herein. The preferred identity of Y in Formula III is —N(R$^2$)$_2$. Particularly preferred are such compounds where each R$^2$ is hydrogen.

R$^1$ in Formula III may be hydrogen or lower alkyl. Hydrogen is preferred for R$^1$. Hydrogen and lower alkyl, particularly C$_1$-C$_3$ alkyl are preferred for R$^2$. Hydrogen is particularly preferred.

Preferred compounds are those where one of R$^{3"}$ and R$^{4"}$ is hydrogen and the other is represented by formula (A").

In formula (A"), the moiety —(C(R$^L$)$_2$)$_o$-x-(C(R$^L$)$_2$)$_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, NR$^{10}$, C(=O), CHOH, C(=N—R$^{10}$), CHNR$^7$R$^{10}$, or represents a single bond;

Therefore, when x represents a single bond, the alkylene chain bonded to the ring is represented by the formula —(C(R$^L$)$_2$)$_{o+p}$—, in which the sum o+p is from 1 to 10.

The preferred R$^L$ groups include —H, —OH, —N(R$^7$)$_2$, especially where each R$^7$ is hydrogen.

In the alkylene chain in formula (A"), it is preferred that when one R$^L$ group bonded to a carbon atoms is other than hydrogen, then the other R$^L$ bonded to that carbon atom is hydrogen, i.e., the formula —CHR$^L$—. It is also preferred that at most two R$^L$ groups in an alkylene chain are other than hydrogen, where in the other R$^L$ groups in the chain are hydrogens. Even more preferably, only one R$^L$ group in an alkylene chain is other than hydrogen, where in the other R$^L$ groups in the chain are hydrogens. In these embodiments, it is preferable that x represents a single bond.

In another particular embodiment of the invention, all of the R$^L$ groups in the alkylene chain are hydrogen. In these embodiments, the alkylene chain is represented by the formula —(CH$_2$)$_o$-x-(CH$_2$)$_p$—.

Each R$^{5'}$ in Formula III may be, independently, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$R$^7$, —O—(CH$_2$)$_m$(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

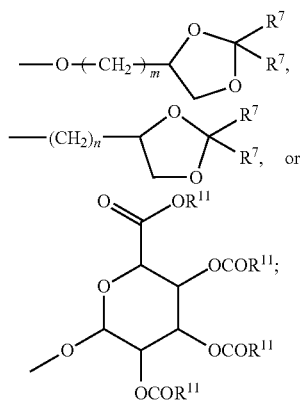

In a preferred embodiment of Formula III, each —(CH$_2$)$_n$—(Z)$_g$—R$^7$ falls within the scope of the structures described above and is, independently,
—(CH$_2$)$_n$—(C=N)—NH$_2$,
—(CH$_2$)$_n$—NH—C(=NH)NH$_2$,
—(CH$_2$)$_n$—CONHCH$_2$(CHOH)$_n$—CH$_2$OH,
—NH—C(=O)—CH$_2$—(CHOH)CH$_2$OH.

In another a preferred embodiment of Formula III, each —O—(CH$_2$)$_m$—(Z)$_g$—R$^7$ falls within the scope of the structures described above and is, independently,
—O—(CH$_2$)$_M$—NH—C(=NH)—N(R$^7$)$_2$,
—O—(CH$_2$)$_m$—CHNH$_2$—CO$_2$NR$^7$R$^{10}$.

In another preferred embodiment, R$^{5'}$ in Formula III may be within the scope of the groups described above as follows:
—O—CH$_2$CHOHCH$_2$O-glucuronide,
—OCH$_2$CHOHCH$_3$,
—OCH$_2$CH$_2$NH$_2$,
—OCH$_2$CH$_2$NHCO(CH$_3$)$_3$,
—CH$_2$CH$_2$OH,
—OCH$_2$CH$_2$OH,
—O—(CH$_2$)$_m$-Boc,
—(CH$_2$)$_m$-Boc,
—OCH$_2$CH$_2$OH,
—OCH$_2$CO$_2$H,
—O(CH$_2$)$_m$NH—C(=NH)—N(R)$_2$,
—NHCH$_2$(CHOH)$_2$—CH$_2$OH,
—OCH$_2$CO$_2$Et,
—NHSO$_2$CH$_3$,
—(CH$_2$)$_m$NH—C(=O)—OR$^7$,
—O(CH$_2$)$_m$—NH—C(=O)—OR$^7$,
—(CH$_2$)NHC(O)R$^{11}$,
—O—CH$_2$C(=O)NH$_2$,
—CH$_2$NH$_2$,
—NHCO$_2$Et,
—OCH$_2$CH$_2$CH$_2$OH, —CH$_2$NHSO$_2$CH$_3$,
—OCH$_2$CH$_2$CHOHCH$_2$OH,
—OCH$_2$CH$_2$NHCO$_2$Et,
—NH—C(=NH$_2$)—NH$_2$,
OCH$_2$-(α-CHOH)$_2$—CH$_2$OH
—OCH$_2$CHOHCH$_2$NH$_2$, —(CH$_2$)$_m$—CHOH—CH$_2$—NHBoc,
—O—(CH$_2$)$_m$—CHOH—CH$_2$—NHBoc,
—(CH$_2$)$_m$NHC(O)OR$^7$,
—O—(CH$_2$)$_m$—NHC(O)OR$^7$,
—OCH$_2$CH$_2$CH$_2$NH$_2$,
—OCH$_2$CH$_2$NHCH$_2$(CHOH)$_2$CH$_2$OH,
—OCH$_2$CH$_2$NH(CH$_2$[(CHOH)$_2$CH$_2$OH)]$_2$,
—(CH$_2$)$_4$—NHBoc,
—OCH$_2$CH$_2$NHSO$_2$CH$_3$,
—O—(CH$_2$)$_m$—C(=NH)—N(R$^7$)$_2$,
—(CH$_2$)—C(=NH)—N(R$^7$)$_2$,
—(CH$_2$)$_3$—NH Boc,
—(CH$_2$)$_3$NH$_2$,
—O—(CH$_2$)$_m$NH—NH—C(=NH)—N(R$^7$)$_2$,
—(CH$_2$)—NH—NH—C(=NH)—N(R$^7$)$_2$, or
—O—CH$_2$—CHOH—CH$_2$—NH—C(=NH)—N(R$^7$)$_2$.

There are four R$^{6''}$ groups present on the ring in formula (A'). Each R$^{6''}$ may be each, independently, —R$^7$, —OR$^{11}$, —N(R$^7$)$_2$, —(CH$_2$)$_m$—OR$^8$, —O(CH$_2$)$_m$OR$^8$, —(CH$_2$)$_n$—NR$^7$R$^{10}$, —O(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O(CH$_2$CH$_2$O)$_m$—CH$_2$CH$_2$NR$^7$R$^{10}$, —(CH$_2$)$_n$—C(=)NR$^9$R$^{10}$, —O(CH$_2$)$_m$C(=O)NR$^9$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —(CH$_2$)$_m$NR$^{10}$—CH$_2$(CHOR$^8$)(CHOR$^8$)$_n$—CH$_2$OR$^8$, —(CH$_2$)$_n$—CO$_2$R$^7$, —O(CH$_2$)$_m$—CO$_2$R$^7$, —OSO$_3$H, —O—glucuronide, —O-glucose, or

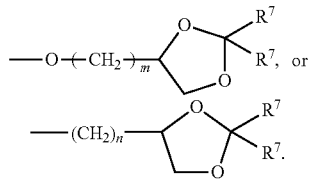

In addition, one of more of the R$^{6''}$ groups can be one of the R$^{5'}$ groups which fall within the broad definition of R$^{6''}$ set forth above.

When two R$^{6''}$ are —OR$^{11}$ and are located adjacent to each other on a phenyl ring, the alkyl moieties of the two R$^{6''}$ groups may be bonded together to form a methylenedioxy group, i.e., a group of the formula —O—CH$_2$—O—.

As discussed above, R$^{6''}$ may be hydrogen. Therefore, 1, 2, 3, or 4 R$^{6''}$ groups may be other than hydrogen. Preferably at most 3 of the R$^{6''}$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n maybe 0, 1, 2, 3, 4, 5, 6, or 7.

Each Q" in formula (A") is C—R$^{5'}$, C—R$^{6''}$, or a nitrogen atom, where at most three Q" in a ring are nitrogen atoms. Thus, there may be 1, 2, or 3 nitrogen atoms in a ring. Preferably, at most two Q" are nitrogen atoms. More preferably, at most one Q" is a nitrogen atom. In one particular embodiment, the nitrogen atom is at the 3-position of the ring. In another embodiment of the invention, each Q" is either C—R$^{5'}$ or C—R$^{6''}$, i.e., there are no nitrogen atoms in the ring.

More specific examples of suitable groups represented by formula (A") are shown in formulas (B')-(E') below:

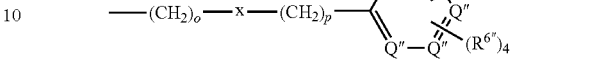
(B')

where o, x, p, R$^{5'}$, and R$^{6''}$, are as defined above;

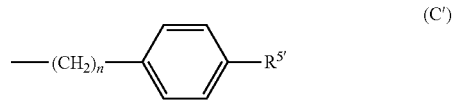
(C')

where n is an integer from 1 to 10 and R$^{5'}$ is as defined above;

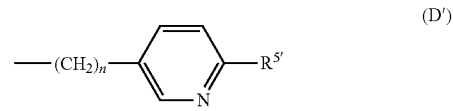
(D')

where n is an integer from 1 from 10 and R$^{5'}$ is as defined above;

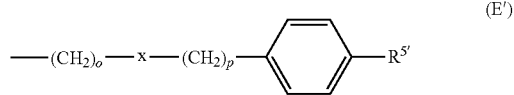
(E')

where o, x, p, and R$^{5'}$ are as defined above.

In a preferred embodiment of Formula III, Y is —NH$_2$.
In another preferred embodiment of Formula III, R$^2$ is hydrogen.
In another preferred embodiment of Formula III, R$^1$ is hydrogen.
In another preferred embodiment of Formula III, X is chlorine.
In another preferred embodiment of Formula III, R$^3$ is hydrogen.
In another preferred embodiment of Formula III, R$^L$ is hydrogen.
In another preferred embodiment of Formula III, o is 4.
In another preferred embodiment of Formula III, p is 0.
In another preferred embodiment of Formula III, the sum of o and p is 4.
In another preferred embodiment of Formula III, x represents a single bond.
In another preferred embodiment of Formula III, R$^{6''}$ is hydrogen.
In another preferred embodiment of Formula III, at most one Q" is a nitrogen atom.
In another preferred embodiment of Formula III, no Q" is a nitrogen atom.
In a preferred embodiment of Formula III:
X is halogen;
Y is —N(R$^7$)$_2$;

$R^1$ is hydrogen or $C_1$-$C_3$ alkyl;

$R^2$ is —$R^7$, —$OR^7$, $CH_2O^7$, or —$CO_2R^7$;

$R^{3''}$ is a group represented by formula (A''); and $R^{4''}$ is hydrogen, a group represented by formula (A''), or lower alkyl.

In another preferred embodiment of Formula III:

X is chloro or bromo;

Y is —$N(R^7)_2$;

$R^2$ is hydrogen or $C_1$-$C_3$ alkyl;

at most three $R^{6''}$ are other than hydrogen as described above;

at most three $R^L$ are other than hydrogen as described above; and at most 2 Q'' are nitrogen atoms.

In another preferred embodiment of Formula III:

Y is —$NH_2$.

In another preferred embodiment of Formula III:

$R^{4''}$ is hydrogen;

at most one $R^L$ is Other than hydrogen as described above;

at most two $R^{6''}$ are other than hydrogen as described above; and at most 1 Q'' is a nitrogen atom.

In another preferred embodiment of Formula III, the compound is

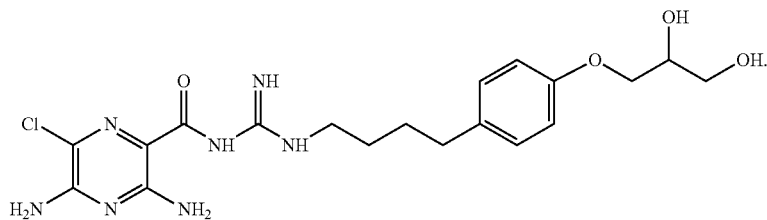

In other preferred embodiments of Formula III, the compound is

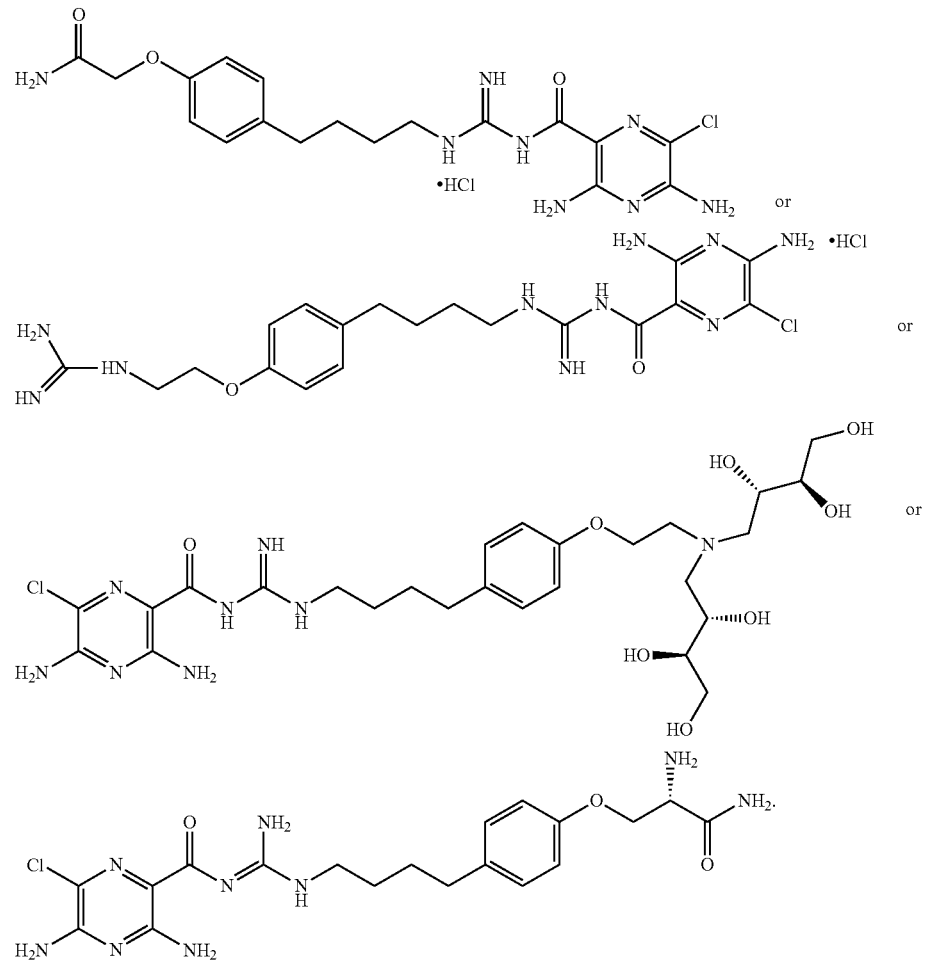

The term sodium channel blocker as used herein includes the free base and pharmaceutically acceptable salts thereof. Pharmaceutically acceptable salts are salts that retain the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formulas (I), (II) and (III) are embraced by the present invention and are included within any reference to Formulas (I), (II) or (III). Additionally, all mixtures of such enantiomers and diastereomers are within the scope of the present invention and are included within any reference to Formulas (I), (II) or (III).

The active compounds disclosed herein may be administered to the lungs of a patient by any suitable means but are preferably administered by administering an aerosol suspension of respirable particles comprised of the active compound, which the subject inhales. The compounds may be inhaled through the mouth or the nose. The active compound can be aerosolized in a variety of forms, such as, but not limited to, dry powder inhalants, metered dose inhalants or liquid/liquid suspensions. The quantity of sodium channel blocker included may be an amount sufficient to achieve the desired effect and as described in the attached applications.

Solid or liquid particulate sodium channel blocker prepared for practicing the present invention should include particles of respirable size: that is, particles of a size sufficiently small to pass through the mouth and larynx upon inhalation and into the bronchi and alveoli of the lungs. In general, particles ranging from about 1 to 5 microns in size (more particularly, less than about 4.7 microns in size) are respirable. Particles of non-respirable size which are included in the aerosol tend to be deposited in the throat and swallowed, and the quantity of non-respirable particles in the aerosol is preferably minimized. For nasal administration, a particle size in the range of 10-500 μm is preferred to ensure retention in the nasal cavity. Nasal administration may be useful where the pathogen typically enters through the nose. However, it is preferred to administer at least a portion of the sodium channel blocker in a dosage form which reaches the lungs to ensure effective prophylactic treatment in cases where the pathogen is expected to reach the lungs.

The dosage of active compound will vary depending on the prophylactic effect desired and the state of the subject, but generally may be an amount sufficient to achieve dissolved concentrations of active compound on the airway surfaces of the subject as described in the attached applications. Depending upon the solubility of the particular formulation of active compound administered, the daily dose may be divided among one or several unit dose administrations. The dosage may be provided as a prepackaged unit by any suitable means (e.g., encapsulating in a gelatin capsule).

Pharmaceutical formulations suitable for airway administration include formulations of solutions, emulsions, suspensions and extracts. See generally, J. Naim, Solutions, Emulsions, Suspensions and Extracts, in *Remington: The Science and practice of Pharmacy*, chap. 86 ($19^{th}$ ed. 1995). Pharmaceutical formulations suitable for nasal administration may be prepared as described in U.S. Pat. Nos. 4,389,393 to Schor; 5,707,644 to Illum, 4,294,829 to Suzuki, and 4,835,142 to Suzuki.

In the manufacture of a formulation according to the invention, active agents or the physiologically acceptable salts or free bases thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a capsule, which may contain from 0.5% to 99% by weight of the active compound. One or more active compounds may be incorporated in the formulations of the invention, which formulations may be prepared by any of the well-known techniques of pharmacy consisting essentially of admixing the components.

Aerosols or mists of liquid particles comprising the active compound may be produced by any suitable means, such as, for nasal administration, by a simple nasal spray with the active compound in an aqueous pharmaceutically acceptable carrier such as sterile saline solution or sterile water. Other means include producing aerosols with a pressure-driven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers may consist of the active ingredient in a liquid carrier. The carrier is typically water (and most preferably sterile, pyrogen-free water) or a dilute aqueous alcoholic solution, preferably made isotonic with body fluids by the addition of, for example, sodium chloride.

Aerosols or mists of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. Such aerosol generators are known in the art. By way of example, see U.S. Pat. No. 5,725,842.

One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant.

A second type of illustrative aerosol generator comprises a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume, typically from 10 to 150 µl to produce a fine particle spray containing the active ingredient. Any propellant may be used in carrying out the present invention, including both chlorofluorocarbon-containing propellants and non-chlorofluorocarbon-containing propellants. Suitable propellants include certain chlorofluorocarbon compounds, for example, dichlorodifluoromethane, trichlorofluoromethane, dichlorotetrafluoroethane and mixtures thereof.

The formulation may additionally contain one or more co-solvents, for example, ethanol, surfactants, such as oleic acid or sorbitan trioleate, antioxidants, preservatives such as methyl hydroxybenzoate, volatile oils, buffering agents and suitable flavoring agents.

Compositions containing respirable dry particles of sodium channel blockers as described in the attached applications may be prepared as detailed in those applications. The active compound may be formulated alone (i.e., the solid particulate composition may consist essentially of the active compound) or in combination with a dispersant, diluent or carrier, such as sugars (i.e., lactose, sucrose, trehalose, mannitol) or other acceptable excipients for lung or airway delivery, which may be blended with the active compound in any suitable ratio (e.g., a 1 to 1 ratio by weight). The dry powder solid particulate compound may be obtained by methods known in the art, such as spray-drying, milling, freeze-drying, and the like.

The aerosol or mist, whether formed from solid or liquid particles, may be produced by the aerosol generator at a rate of from about 10 to about 150 liters per minute, more preferably from about 30 to about 150 liters per minute, and most preferably about 60 liters per minute. Aerosols containing greater amounts of medicament may be administered more rapidly.

Other medicaments may be administered with the active compounds disclosed if such medicament is compatible with the active compound and other ingredients in the formulation and can be administered as described herein.

The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism.

The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality.

Category A: *Bacillus anthracis* (anthrax),
   *Clostridium botulinum* (botulism),
   *Yersinia pestis* (plague),
   *Variola major* (smallpox) and other pox viruses,
   *Francisella tularensis* (tularemia),
   Viral hemorrhagic fevers
   Arenaviruses,
     LCM (lymphocytic choriomeningitis), Junin virus,
   Machupo virus, Guanarite virus,
     Lassa Fever,
     Bunyaviruses,
     Hantavirus,
     Rift Valley Fever,
   Flaviviruses,
     Dengue,
   Filoviruses,
     Ebola
     Marburg;
Category B: *Burkholderia pseudomallei* (melioidosis),
   *Coxiella burnetii* (Q fever),
   *Brucella* species (brucellosis),
   *Burkholderia mallei* (glanders),
   Ricin toxin from *Ricinus communis,*
   Epsilon toxin of *Clostridium perfringens,*
   Staphylococcal enterotoxin B,
   Typhus fever (*Rickettsia prowazekii*),
   Food and water-borne pathogens
     bacteria:
       Diarrheagenic *Escherichia coli,*
       Pathogenic vibrios,
       *Shigella* species,
       *Salmonella* species,
       *Listeria monocytogenes,*
       *campylobacter jejuni,*
       *Yersinia enterocolitica;*
   Viruses
     Caliciviruses,
     Hepatitis A;
   Protozoa
     *Cryptosporidium parvum,*
     *Cyclospora cayatenensis,*
     *Giardia lamblia,*
     *Entamoeba histolytica,*
     *Toxoplasma,*
     *Microsporidia,* and
   Additional viral encephalitides
     West Nile virus,
     LaCrosse,
     California encephalitis,
     Venezuelan equine encephalitis,
     Eastern equine encephalitis,
     Western equine encephalitis,
     Japanese encephalitis virus and
     Kyasanur forest virus, and
Category C: emerging infectious disease threats such as Nipah virus and additional hantaviruses, tickborne hemorrhagic fever viruses such as Crimean Congo hemorrhagic fever virus, tickborne encephalitis viruses, yellow fever, multi-drug resistant tuberculosis, influenza, other rickettsias and rabies.

Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

A number of the above-listed pathogens are known to be particularly harmful when introduced into the body through the air. For example, *Bacillus anthracis*, the agent which causes anthrax, has three major clinical forms, cutaneous, inhalational, and gastrointestinal. All three forms may lead to death but early antibiotic treatment of cutaneous and gastrointestinal anthrax usually cures those forms of anthrax. Inhalational anthrax, on the other hand, is a potentially fatal disease even with antibiotic treatment. Initial symptoms may resemble a common cold. After several days, the symptoms may progress to severe breathing problems and shock. For naturally occurring or accidental infections, even with appropriate antibiotics and all other available supportive care, the historical fatality rate is believed to be about 75 percent, according to the NIAID. Inhalational anthrax develops after spores are deposited in alveolar spaces and subsequently ingested by pulmonary alveolar macrophages. Surviving spores are then transported to the mediastinal lymph nodes, where they may germinate up to 60 days or longer. After germination, replicating bacteria release toxins that result in disease. This process is interrupted by administration of a prophylactically effective amount of a sodium channel blocker, as the spores may be wholly or partially eliminated from the body by removal of lung mucous secretions hydrated through the action of the sodium channel blocker.

Another pathogen of primary concern as one of the most dangerous potential biological weapons because it is easily transmitted from person to person, no effective therapy exists and few people carry full immunity to the virus, is the small pox virus, *Variola major*. Smallpox spreads directly from person to person, primarily by aerosolized saliva droplets expelled from an infected person. Initial symptoms include high fever, fatigue, headache and backache followed in two or three days by a characteristic rash.

The present invention provides a method of prophylactically treating one or more individuals exposed or potentially exposed to smallpox virus or other pox virus comprising the administration of a prophylactically effective amount of a sodium channel blocker. The administration of an effective amount of a sodium channel blocker will function to allow the *Variola major* virus or other pox virus present in the aerosolized saliva droplets to which the individual was exposed to be wholly or partially removed from the body by removal of hydrated lung mucous secretions hydrated through the action of the sodium channel blocker.

The bacterium *Yersinia pestis* causes plague and is widely available throughout the world. NIAID has reported that infection by inhalation of even small numbers of virulent aerosolized *Y. pestis* bacilli can lead to pneumonic plague, which has a mortality rate of almost 100% if left untreated. Pneumonic plague has initial symptoms of fever and cough which resemble other respiratory illnesses. Antibiotics are effective against plague but success with antibiotics depends on how quickly drug therapy is started, the dose of inhaled bacteria and the level of supportive care for the patient; an effective vaccine is not widely available.

The present invention provides a method of prophylactically treating one or more individuals exposed or potentially exposed to aerosolized *Y. pestis* bacilli comprising the administration of a sodium channel blocker. The administration of an effective amount of a sodium channel blocker will function to allow the aerosolized *Y. pestis* bacilli to be wholly or partially removed from the body by removal of hydrated lung mucous secretions hydrated through the action of the sodium channel blocker.

Botulinum toxin is another substance believed to present a major bioterrorism threat as it is easily released into the environment. Antibiotics are not effective against botulinum toxin and no approved vaccine exists. Although the toxin may be transmitted through food, the botulinum toxin is absorbed across mucosal surfaces and, thus, the present invention provides a method of prophylactically treating one or more individuals exposed or potentially exposed to botulinum toxin comprising the administration of a sodium channel blocker.

The NIAID has identified the bacteria that causes tularemia as a potential bioterrorist agent because *Francisella tularensis* is capable of causing infection with as few as ten organisms and due to its ability to be aerosolized. Natural infection occurs after inhalation of airborne particles. Tularemia may be treated with antibiotics and an experimental vaccine exists but knowledge of optimal therapeutic approaches for tularemia is limited because very few investigators are working on this disease. The present invention provides a method of prophylactically treating one or more individuals exposed or potentially exposed to aerosolized *Francisella tularensis* comprising the administration of a sodium channel blocker. The administration of an effective amount of a sodium channel blocker will function to allow the aerosolized *Francisella tularensis* to be wholly or partially removed from the body by removal of hydrated lung mucous secretions hydrated through the action of the sodium channel blocker.

The Category B and C bacteria most widely believed to have the potential to infect by the aerosol route include gram negative bacteria such as *Brucella* species, *Burkholderia pseudomallei, Burkholderia mallei, Coxiella burnetii*, and select *Rickettsia* spp. Each of these agents is believed to be capable of causing infections following inhalation of small numbers of organisms. *Brucella* spp. may cause brucellosis. Four of the six *Brucella* spp., *B. suis, B. melitensis, B. abortus* and *B. canis*, are known to cause brucellosis in humans. *Burkholderia pseudomallei* may cause melioidosis in humans and other mammals and birds. *Burkholderia mallei*, is the organism that causes glanders, normally a disease of horses, mules and donkeys but infection following aerosol exposure has been reported, according to NIAID. *Coxiella burnetii*, may cause Q fever and is highly infectious. Infections have been reported through aerosolized bacteria and inhalation of only a few organisms can cause infections. *R. prowazekii, R. rickettsii, R. conorrii* and *R. typhi* have been found to have low-dose infectivity via the aerosol route.

The present invention provides a method of prophylactically treating one or more individuals exposed or potentially exposed to aerosolized gram negative bacteria such as *Brucella* species, *Burkholderia pseudomallei, Burkholderia mallei, Coxiella burnetii*, and select *Rickettsia* spp comprising the administration of a sodium channel blocker. The administration of an effective amount of a sodium channel blocker will function to allow the aerosolized gram negative bacteria to be wholly or partially removed from the body by removal of hydrated lung mucous secretions hydrated through the action of the sodium channel blocker.

A number of typically arthropod-borne viruses are believed to pose a significant threat as potential bioterrorist weapons due to their extreme infectivity following aerosolized exposure. These viruses include arboviruses which are important agents of viral encephalitides and hemorrhagic fevers. Such viruses may include alphaviruses such as Venezuelan equine encephalitis virus, eastern equine encephalitis virus and western equine encephalitis virus. Other such viruses may include flaviviruses such as West Nile virus, Japanese encephalitis virus, Kyasanur forest disease virus, tick-borne encephalitis virus complex and yellow fever virus. An additional group of viruses which may pose a threat include bunyaviruses such as California encephalitis virus, or La Crosse virus, Crimean-Congo hemorrhagic fever virus. According to the NIAID, vaccines or effective specific therapeutics are available for only a very few of these viruses. In humans, arbovirus infection is usually initially asymptomatic or causes nonspecific flu-like symptoms such as fever, aches and fatigue.

The present invention provides a method of prophylactically treating one or more individuals exposed or potentially exposed to aerosolized arboviruses comprising the administration of a sodium channel blocker. The administration of an effective amount of a sodium channel blocker will function to allow the arboviruses to be wholly or partially removed from the body by removal of hydrated lung mucous secretions hydrated through the action of the sodium channel blocker.

Certain category B toxins such as ricin toxin from *Ricinus communis*, epsilon toxin of *Clostridium perfringens* and Staphylococcal enterotoxin B, also are viewed as potential bioterrorism tools. Each of these toxins may be delivered to the environment or population by inhalational exposure to aerosols. Low dose inhalation of ricin toxin may cause nose and throat congestion and bronchial asthma while higher dose inhalational exposure caused severe pneumonia, acute inflammation and diffuse necrosis of the airways in nonhuman primates. *Clostridium perfringens* is an anaerobic bacterium that can infect humans and animals. Five types of bacteria exist that produce four major lethal toxins and seven minor toxins, including alpha toxin, associated with gas gangrene, beta toxin, responsible for necrotizing enteritis, and epsilon toxin, a neurotoxin that leads to hemorrhagic enteritis in goats and sheep. Inhalation of *Staphylococcus aureus* has resulted in extremely high fever, difficulty breathing, chest pain and headache.

The present invention provides a method of prophylactically treating one or more individuals exposed or potentially exposed to aerosolized toxins comprising the administration of a sodium channel blocker. The administration of an effective amount of a sodium channel blocker will function to allow the aerosolized toxins to be wholly or partially removed from the body by removal of hydrated lung mucous secretions hydrated through the action of the sodium channel blocker.

*Mycobacterium tuberculosis* bacteria causes tuberculosis and is spread by airborne droplets expelled from the lungs when a person with tuberculosis coughs, sneezes or speaks. The present invention provides a method of prophylactically treating one or more individuals exposed or potentially exposed to *Mycobacterium tuberculosis* bacteria comprising the administration of a sodium channel blocker. The administration of an effective amount of a sodium channel blocker will function to allow the *Mycobacterium tuberculosis* bacteria to be wholly or partially removed from the body by removal of hydrated lung mucous secretions hydrated through the action of the sodium channel blocker.

The methods of the present invention may also be used against more common pathogens such as influenza viruses, rhinoviruses, adenoviruses and respiratory syncytial viruses (RSV). The present invention provides a method of prophylactically or therapeutically treating one or more individuals exposed or potentially exposed to one of these viruses comprising the administration of a sodium channel blocker. The administration of an effective amount of a sodium channel blocker will function to allow the virus to be wholly or partially removed from the body by removal of hydrated lung mucous secretions hydrated through the action of the sodium channel blocker.

The methods of the present invention may further be used against the virus believed to be responsible for SARS, the coronavirus. Severe acute respiratory syndrome is a respiratory illness that is believed to spread by person-to-person contact, including when someone coughs or sneezes droplets containing the virus onto others or nearby surfaces. The CDC currently believes that it is possible that SARS can be spread more broadly through the air or by other ways that are not currently known. Typically, SARS begins with a fever greater than 100.4° F. Other symptoms include headache and body aches. After two to seven days, SARS patients may develop a dry cough and have trouble breathing.

To the extent SARS is caused by an airborne pathogen, the present invention provides a method of prophylactically treating one or more individuals exposed or potentially exposed to the SARS virus comprising the administration of a sodium channel blocker. The administration of an effective amount of a sodium channel blocker will function to allow the virus to be wholly or partially removed from the body by removal of hydrated lung mucous secretions hydrated through the action of the sodium channel blocker.

The compounds of formulas (I), (II) and (III) may be synthesized according to procedures known in the art. A representative synthetic procedure is shown in the scheme below:

$$\underset{Y}{\overset{X}{\bigvee}}\overset{N}{\underset{NHR^2}{\bigvee}}\overset{O}{\underset{N=C-S-CH_3}{\bigvee}}\overset{NHR^1}{\underset{}{\mid}} + HNR^3R^4 \longrightarrow (I)$$

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813.

Several assays may be used to characterize the compounds of the present invention. Representative assays are discussed below.

In Vitro Measure of Sodium Channel Blocking Activity and Reversibility

One assay used to assess mechanism of action and/or potency of the compounds of (I), (II), and (III) involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Ussing chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at $-20°$ C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls.

Pharmacological Assays of Absorption (1) Apical Disappearance Assay

Bronchial cells (dog, human, sheep, or rodent cells) are seeded at a density of $0.25 \times 10^6/cm^2$ on a porous Transwell-Col collagen-coated membrane with a growth area of 1.13 $cm^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 µl) and is initiated by adding experimental sodium channel blockers or positive controls (amiloride, benzamil, phenamil) to the apical surface at an initial concentration of 10 µM. A series of samples (5 µl volume per sample) is collected at various time points, including 0, 5, 20, 40, 90 and 240 minutes. Concentrations are determined by measuring intrinsic fluorescence of each sodium channel blocker using a Fluorocount Microplate Fluorometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 µl KBR, containing 10 µM test compound) is placed on the epithelial lumenal surface. Sequential 5 to 10 µl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

4. Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

EXAMPLES

Having generally described this invention, a further understanding can be obtained by reference to certain specific examples which are provided herein for purposes of illustration only and are not intended to be limiting unless otherwise specified.

Example 1

The following examples are directed to compounds encompassed by Formula I.

Sodium Channel Blocking Activity

The compounds shown in Tables 1-4 below were tested for potency in canine bronchial epithelia using the in vitro assay described above. Amiloride and/or a compound 33 was also tested in this assay as a positive control. The results for the compounds of the present invention are reported as fold-enhancement values relative to amiloride.

TABLE 1

Cl, pyrazine core with NH₂ groups, C(O)N=C(NH₂)—NH—(CH₂)₄—phenyl with OR substituents · HCl

| Position | R | Fold Enhancement Over Amiloride |
|---|---|---|
| 2,4 | H | 14.9 |
| 3,5 | H | 13.7 |
| 3,4 | H | 15.1 |
| 2,5 | H | 20.3 |

TABLE 2

Cl, pyrazine core, C(O)N=C(NH₂)—NH—(CH₂)$_n$—phenyl—R

| n | Position of R | R | Fold Enhancement Over Amiloride |
|---|---|---|---|
| 5 | 4 | OH | 14 |
| 3 | 4 | OH | 5.2 |
| 4 | 4 | OH | 50.3 |

TABLE 3

Cl, pyrazine core, C(O)N=C(NH₂)—NH—(CH₂)₄—ring with Q and R

| Q | R | Fold Enhancement Over Amiloride |
|---|---|---|
| N | OH | 9.5 |
| CH | OH | 50.3 |

TABLE 4

Cl, pyrazine core, C(O)N=C(NH₂)—NH—CH₂CH₂—a—b—phenyl—OR

| a | b | R | Fold Enhancement Over Amiloride |
|---|---|---|---|
| CH₂ | O | H | 16.1 |

Example 2

Figure 2:
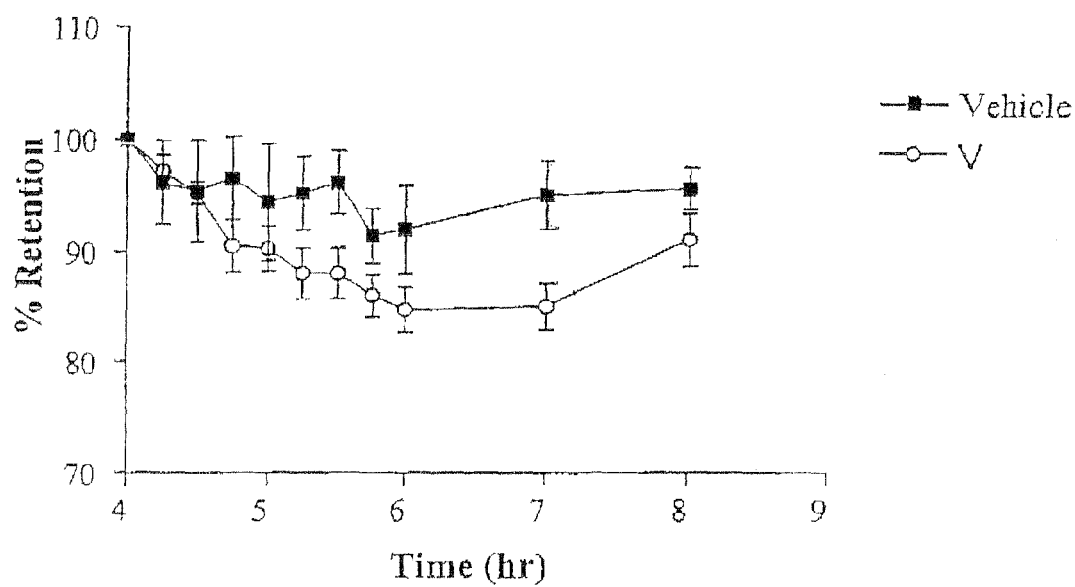
FIG. 2: Effect of a compound of Formula I on MCC at t=4 hrs as described in the Examples herein.

Effect of 4-(4-hydroxyphenyl)butylamidino-3,5-diamino-6-chloropyrazinecarboxamide hydrochloride (V) on MCC This experiment was conducted with 4-(4-hydroxyphenyl) butylamidino-3,5-diamino-6-chloropyrazinecarboxamide hydrochloride (V), and the vehicle as a control. The results are shown in FIGS. 1 and 2.

Methods

Animal Preparation: The Mount Sinai Animal Research Committee approved all procedures for the in vivo assessment of mucociliary clearance. Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 µm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess over effects), followed by a paired t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Example 3

The following examples relate to compounds of Formula III:

Sodium Channel Blocking Activity

The compounds shown in the Tables below were tested for potency in canine bronchial epithelia using the in vitro assay described above. Amiloride was also tested in this assay as a positive control. The results for the compounds of the present invention are reported as fold-enhancement values relative to amiloride.

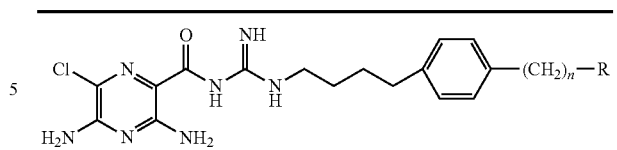

| R = | N = | Fold Amiloride* |
|---|---|---|
| OH | 1 | 50.9 ± 19.8 (3) |
| OH | 2 | 79.2 ± 30.6 (4) |
| OH | 4 | 45.3 ± 27.0 (6) |
| NH$_2$ | 0 | 32.6 ± 2.0 (3) |
| NH$_2$ | 1 | 26.2 ± 5.1 (3) |
| NH$_2$ | 3 | 59 ± 5.5 (4) |
| NH$_2$ | 4 | 132.6 ± 47.2 (5) |

| R = | n = | Fold Amiloride* |
|---|---|---|
| OH | 2 | 84.9 ± 30.3 (6) |
| OH | 3 | 105.2 ± 26.6 (7) |
| OH | 4 | 21 (1) |
| NH$_2$ | 2 | 60.1 ± 1.3 (2) |
| NH$_2$ | 2 | 56.5 ± 0 (4) |
| NH$_2$ | 3 | 102.6 ± 49 (2) |

| X = | Y = | Fold Amiloride* |
|---|---|---|
| C═O | NH$_2$ | 73.1 ± 31.5 (3) |
| C═O | NH(CH$_2$)$_2$—OH | 28.5 (1) |
| C═NH | NH$_2$ | 53.2 ± 19.3 (2) |
| NH | H | 32.6 ± 2 (3) |
| NH | COCH$_3$ | 52.3 ± 16.4 (3) |
| NH | SO$_2$CH$_3$ | 38.5 ± 4.2 (3) |
| NH | CO$_2$C$_2$H$_5$ | 29.0 ± 5.8 (2) |
| NH | C(═NH)NH$_2$ | 88.0 ± 18.0 (2) |

| R = | R$^1$ = | Fold Amiloride* |
|---|---|---|
| OR$^1$ | H | 50.9 ± 19.8 (3) |
| NHR$^1$ | H | 28 (1) |
| NHR$^1$ | COCH$_3$ | 16 (1) |
| NHR$^1$ | SO$_2$CH$_3$ | 50.6 ± 11.9 (2) |
| NHR$^1$ | CO$_2$C$_2$H$_5$ | 24.1 ± 0.5 (3) |
| NHR$^1$ | CO$_2$—(CH$_3$)$_3$ | 29.0 ± 4.1 (2) |
| NHR | C(═NH)NH$_2$ | 66.2 ± 27.4 (4) |

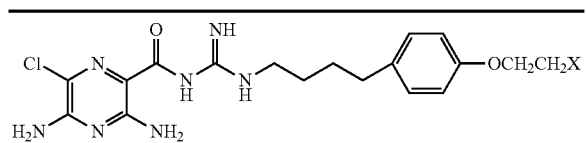

| X = | Fold Amiloride* |
|---|---|
| NH$_2$ | 56.5 ± 24 (4) |
| NH—C(=NH)—NH$_2$ | 120.6 ± 60.8 (11) |
| NHSO$_2$CH$_3$ | 64.0 (1) |
| NHCO$_2$(CH$_3$)$_3$ | 51.7 ± 10.1 (2) |
| NHCOCH$_3$ | 48.5 ± 26.5 (4) |

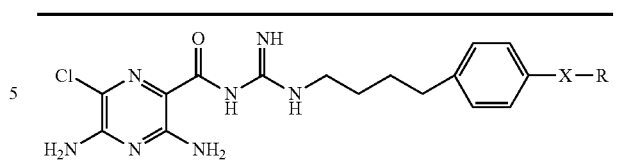

| | | | | | Fold Amiloride* |
|---|---|---|---|---|---|
| NH$_2$ | | | | | 32.6 ± 2 (3) |
| NH | R | | | | 44.9 ± 14.7 (8) |
| O | CH$_2$ | CH$_2$ | NH$_2$ | | 84.9 ± 30.3 (6) |
| O | CH$_2$ | CH$_2$ | NH | R$^a$ | 52.9 ± 14.3 (5) |
| O | CH$_2$ | CH$_2$ | NR | R$^{a,c}$ | 73.2 ± 49.3 (9) |
| O | CH$_2$ | CH$_2$ | O | R$^1$ | 76.1 (1) |
| O | CH$_2$ | CH$_2$ | O | CH$_3$ | 51.5 ± 14.9 (2) |
| O | R | | | | 93.7 ± 42.1 (5) |
| O | CH$_2$ | CHOH | CH$_2$ | OH | 51.95 (79) |
| O | CH$_2$ | CH$_2$ | NR | R$^{a,c}$ | 56.0 (1) |
| O | CH$_2$ | CH$_2$ | NR$^2$ | R$^{2,a}$ | |

R$^2$ = CH$_2$(CHOH)$_3$CH$_2$OH
R = CH$_2$CHOHCHOHCH$_2$OH
R$^1$ = CH$_2$CH$_2$OCH$_3$
$^a$Chiral
$^b$Racemic
$^c$Enantiomers

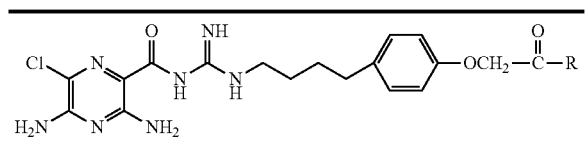

| R = | Fold Amiloride* |
|---|---|
| —OH | 14.0 ± 4.6 (7) |
| —O(CH$_3$)$_3$ | 29.2 ± 10.9 (3) |
| —NH$_2$ | 48.2 ± 24.1 (7) |

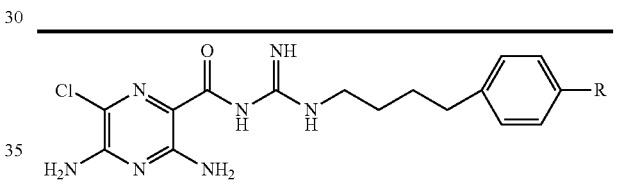

| | | | | | Fold Amiloride* |
|---|---|---|---|---|---|
| CH$_2$ | CH$_2$ | OH | | | 79.2 ± 30.6 (4) |
| O | CH$_2$ | CH$_2$ | OH | | 84.9 ± 30.3 (6) |
| O | CH$_2$ | CH$_2$ | CH$_2$ | OH | 105.2 ± 26.6 (7) |
| CH$_2$ | CH$_2$ | CH$_2$ | CH$_2$ | OH | 37.4 (1) |
| O | CH$_2$ | CHOH | CH$_2$ | OH | 51.95 (50) |
| O | CH$_2$ | CHOH | CH$_2$ | NH$_2$ | 57.5 ± 24.5 (6) |
| O | CH$_2$ | CH$_2$ | CH$_2$ | OH | 21 (1) |
| O | CH$_2$ | CH$_2$ | CHOH | OH | 55.5 ± 19.3 (3) |
| O | CH$_2$ | CHOH | CHOH | OH | 93.7 ± 42.1 (5) |
| O | CH$_2$ | CHOH | CHOH | CH$_2$OH | 56.1 ± 15.6 (4) |
| N | CH$_2$ | CHOH | CHOH | CH$_2$OH | 44.9 ± 14.7 (8) |

| | Fold Amiloride* |
|---|---|
| O(CH$_2$)NHCO$_2^+$ | 51.7 ± 10.1 (2) |
| OCH$_2$CO$_2^+$ | 29.2 ± 10.9 (3) |
| OCH$_2$CO$_2$ET | 20 (1) |
| —NHCH$_2$CO$_2^+$ | 29.0 ± 4.1 (2) |
| NHCO$_2$ET | 29.0 ± 5.38 (2) |
| CH$_2$NHCO$_2$ET | 24.1 ± 0.5 (3) |
| O(CH$_2$)$_2$NHCO$_2$ET | 17.7 ± 6.0 (2) |
| OCH$_2$CHOHCH$_2$NHCO$_2^+$ | 77.9 ± 24.0 (3) |
| O(CH$_2$)$_3$NHCO$_2^+$ | 37.5 ± 12.8 (4) |
| (CH$_2$)$_4$—NHCO$_2^+$ | 16.9 ± 2.3 (2) |

+ = (CH$_3$)$_3$; Boc = —CO$_2$(CH$_3$)$_3$

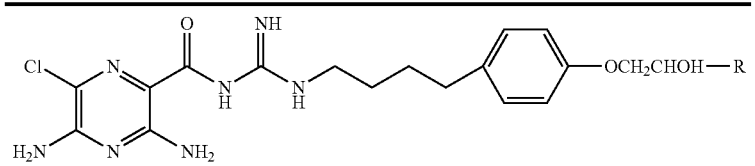

| R = | Position | Fold Amiloride* |
|---|---|---|
| H | Ortho | 21.7 ± 4.8 (2) |
| H | Meta | 41.1 ± 8.5 (2) |
| H | Para | 80.3 ± 25.5 (9) |
| CH$_2$OH | Ortho | 24.0 ± 1.0 (2) |
| CH$_2$OH | Meta | 40 (1) |
| CH$_2$OH | Para | 51.55 (79) |

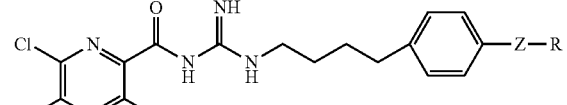

| R=\Z= | H | O(CH₂)₂—R | O(CH₂)₃—R | CH₂R | (CH₂)₃R |
|---|---|---|---|---|---|
| OH Xamiloride | | 84.9 ± 30.3 | 105.2 ± 26.6 | 50.9 ± 19.8 (3) | |

| R=\Z= | H | O(CH₂)₂—R | O(CH₂)₃—R | CH₂R | —(CH₂)₃R |
|---|---|---|---|---|---|
| NH₂ Xamiloride | 32.6 ± 2 | 56.5 ± 0 | 102.6 ± 49 | 26.2 ± 5.1 (3) | 54.4 ± 43.5 (6) |

| R=\Z= | H | O(CH₂)₂—R | O(CH₂)₃—R | CH₂R | (CH₂)₃R |
|---|---|---|---|---|---|
| —NHCNH₂ (NH) Xamiloride | 88.0 ± 18.0 | 98.0 ± 58.5 (18) | 50.2 ± 17.4 (4) | 35 (1) | 47.6 (3) |

Example 4

Effect of 4-[4-(2,3-Dihydroxypropyloxyl)phenyl]butylamidino-3,5-diamino-6-chloropyrazinecarboxamide hydrochloride (33) on MCC

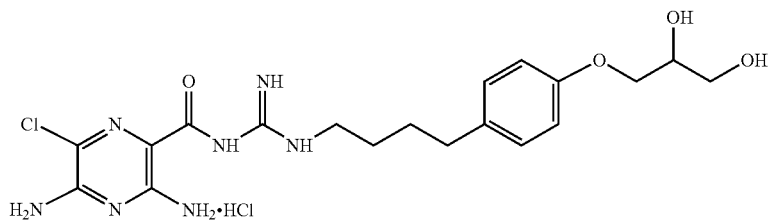

Figure 3:
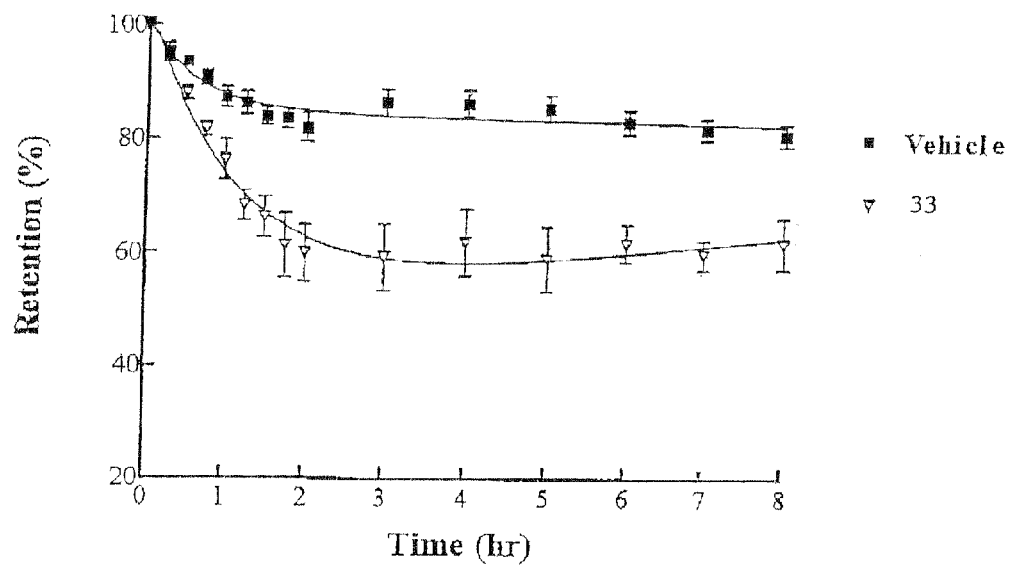
FIG. 3: Effect of a compound of Formula III on MCC at t=0 hrs as described in the Examples herein.
Figure 4:
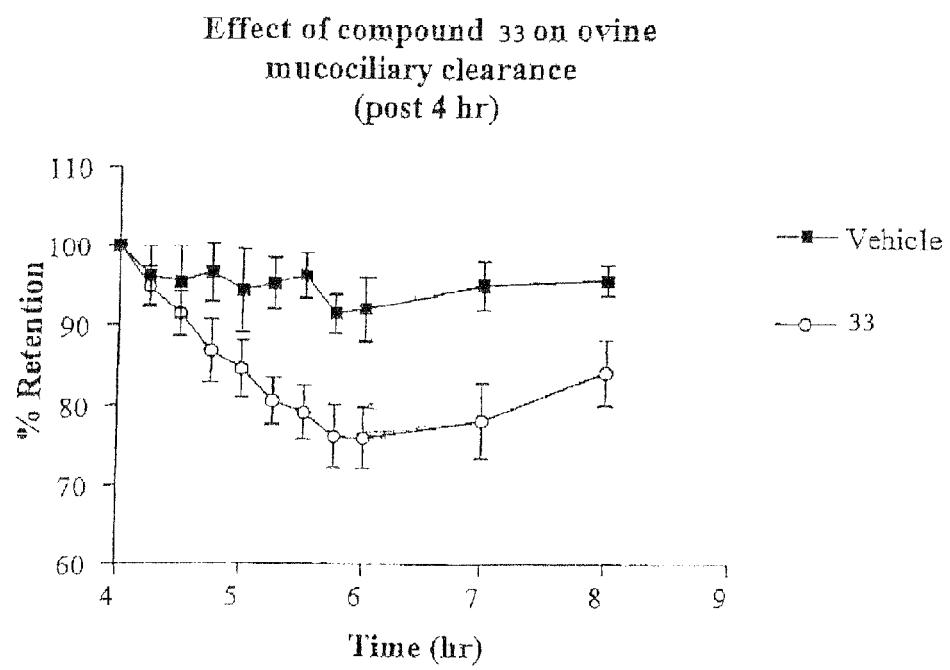
FIG. 4: Effect of a compound of Formula III on MCC at t=4 hrs as described in the Examples herein.

This experiment was conducted with 4-[4-(2,3-Dihydroxypropyloxyl)phenyl]butylamidino-3,5-diamino-6-chloropyrazinecarboxamide hydrochloride (33), and the vehicle as a control. The results are shown in FIGS. 3 and 4.

Methods

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 mm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paired t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Example 5

Effect of Compound 9518 on MCC N-(3,5-diamino-6-chloropyrazine-2-carbonyl)-N'-{4-[4-(2-guanidinoethoxy)-phenyl]butyl}guanidine dihydrochloride (9518)

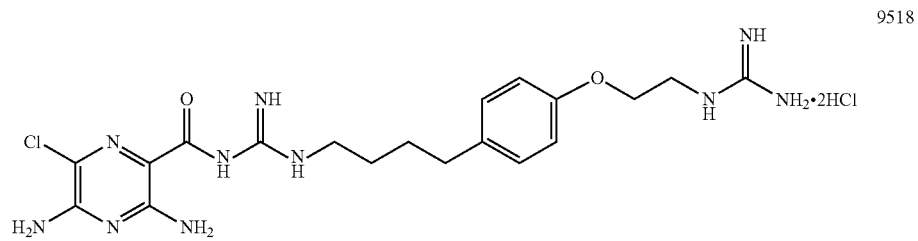

Figure 5:
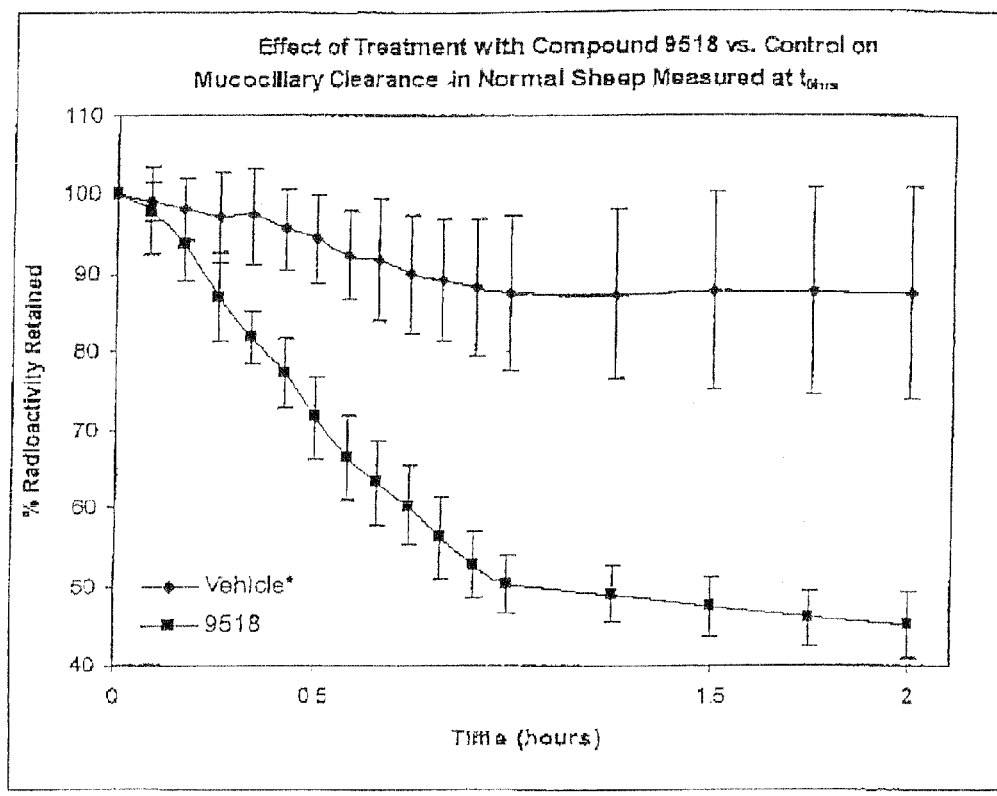
FIG. 5: Effect of a compound of Formula III on MCC at t=0 hrs as described in the Examples herein.
Figure 6:
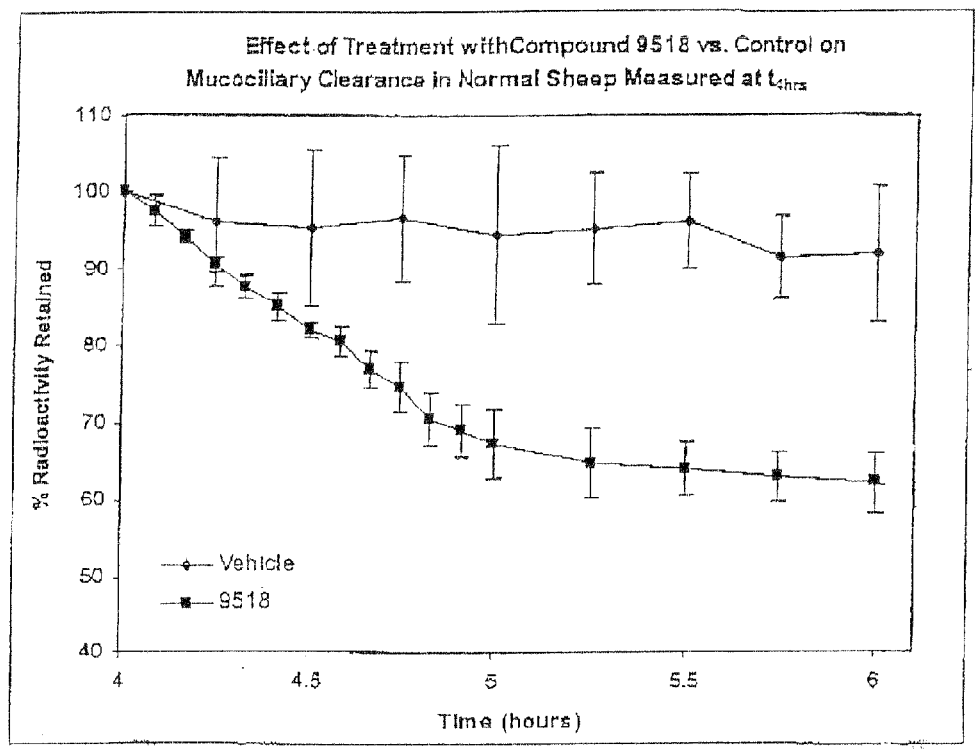
FIG. 6: Effect of a compound of Formula III on MCC at t=4 hrs as described in the Examples herein.

This experiment was conducted according to methods of Example 4 with compound 9518 and the vehicle as a control. The results are shown in FIGS. 5 and 6.

Example 6

Effect of Compound 9714 on MCC 2-{4-[N'-(3,5-diamino-6-chloropyrazine-2-carbonyl)guanidino]-4-butylphenoxy}acetamide hydrochloride (9714)

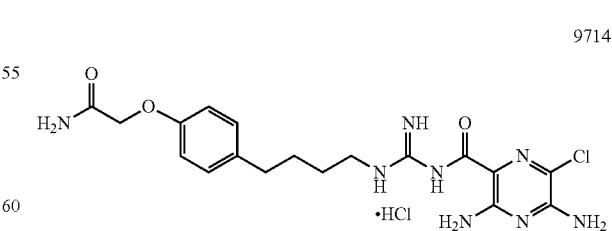

Figure 7:
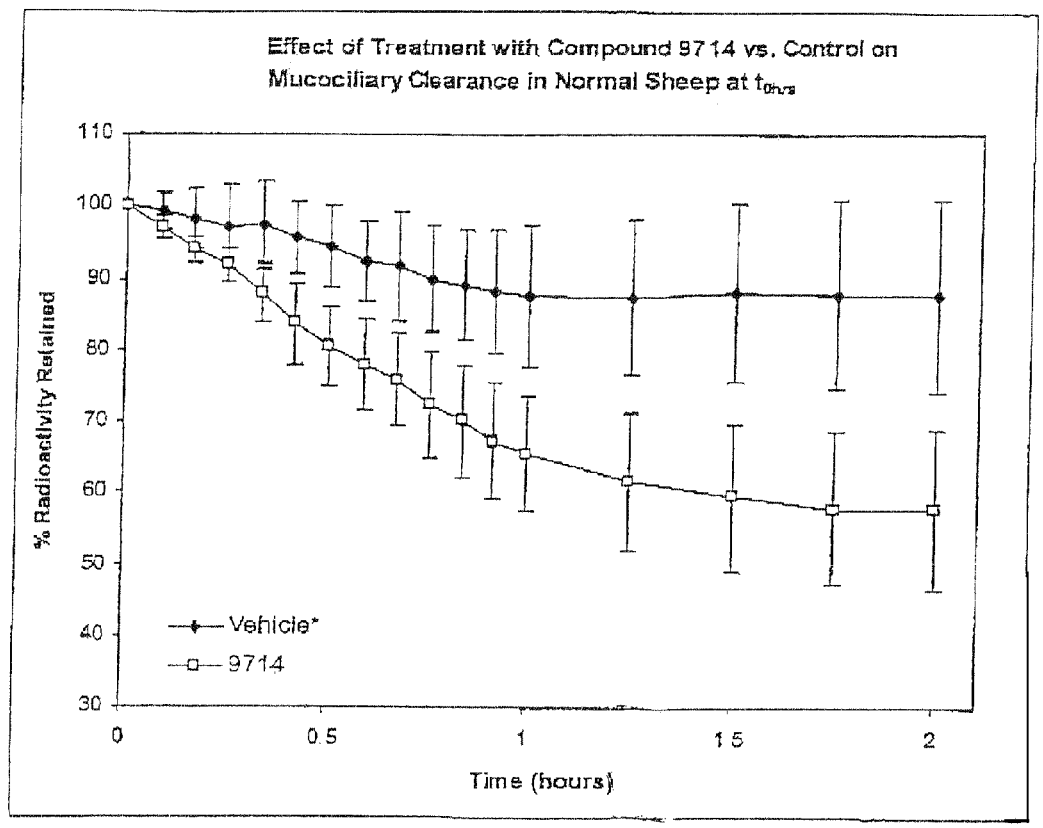
FIG. 7: Effect of a compound of Formula III on MCC at t=0 hrs as described in the Examples herein.
Figure 8:
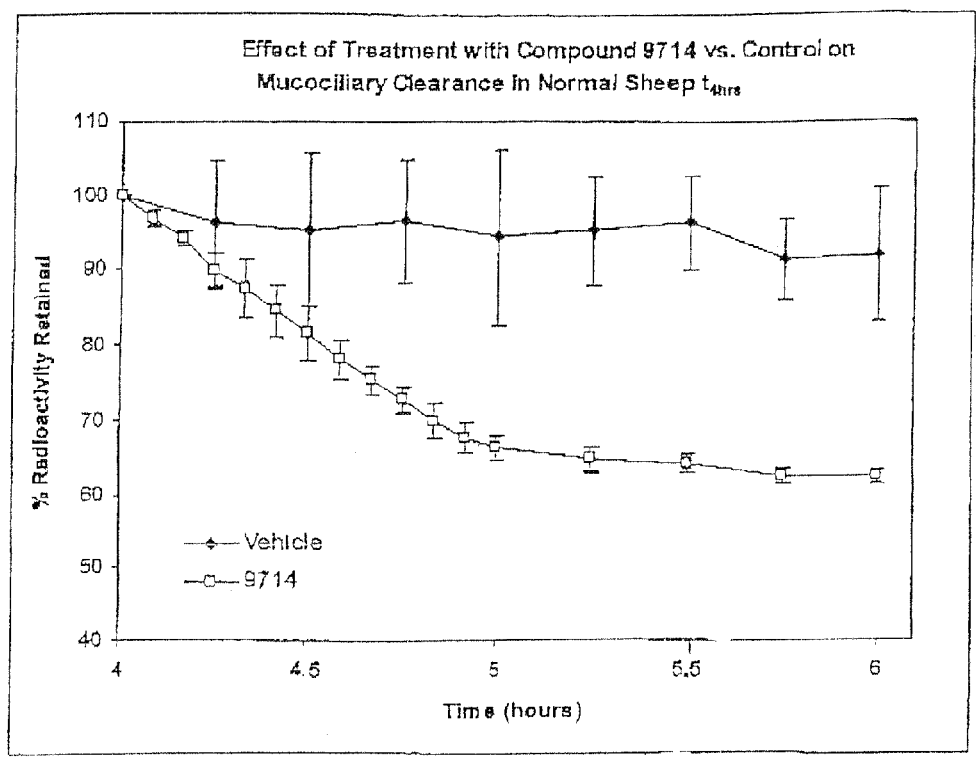
FIG. 8: Effect of a compound of Formula III on MCC at t=4 hrs as described in the Examples herein.

This experiment was conducted according to methods of Example 4 with compound 9714 and the vehicle as a control. The results are shown in FIGS. 7 and 8.

Example 7

Effect of Compound 10833 on MCC N-[4-(4-{2-[bis-((2S,3R)-2,3,4-trihydroxybutyl)amino]ethoxy}phenyl)butyl]-N'-(3,5-diamino-6-chloropyrazine-2-carbonyl)guanidine dihydrochloride (10833)

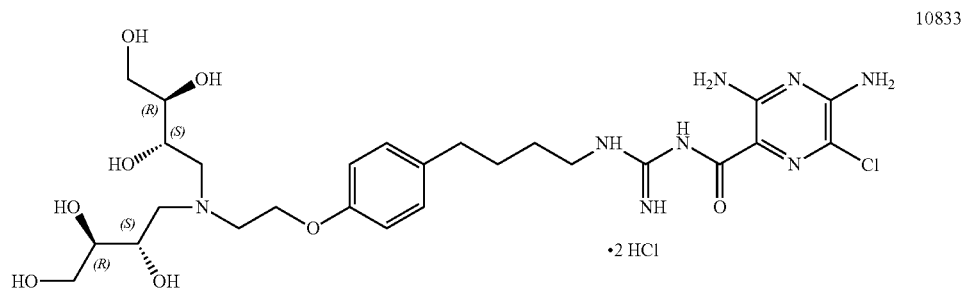

Figure 9:
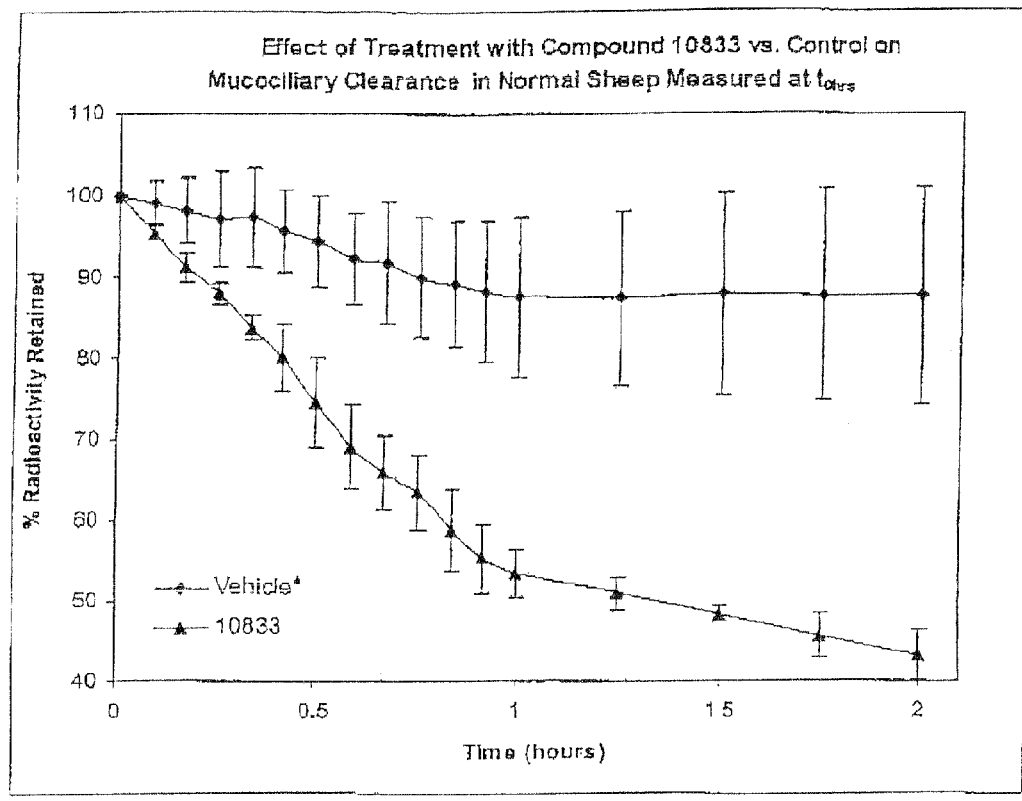
FIG. 9: Effect of a compound of Formula III on MCC at t=4 hrs as described in the Examples herein.
Figure 10:
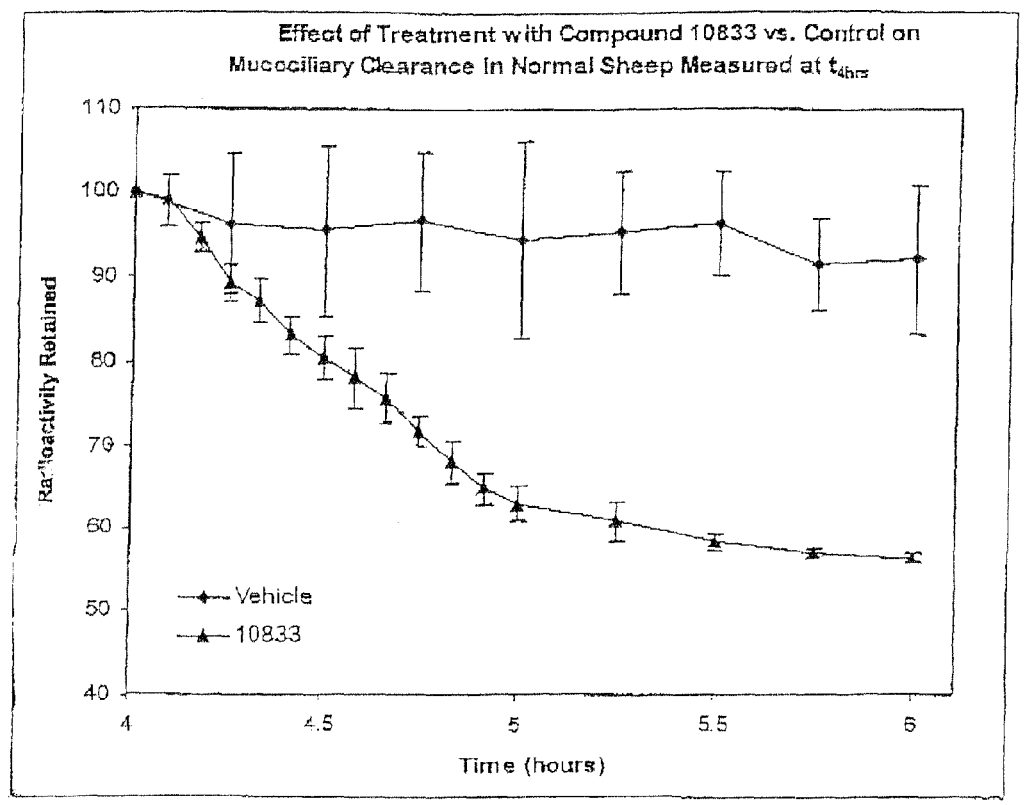
FIG. 10: Effect of a compound of Formula III on MCC at t=4 hrs as described in the Examples herein.

This experiment was conducted according to methods of Example 4 with compound 10833 and the vehicle as a control. The results are shown in FIGS. 9 and 10.

While the invention has been described with reference to preferred aspects, it is to be understood that variations and modifications may be resorted to as will be apparent to those skilled in the art. Such variations and modifications are to be considered within the purview and the scope of the claims appended hereto.

What is claimed is:

1. A compound represented by the formula or a pharmaceutically acceptable salt thereof:

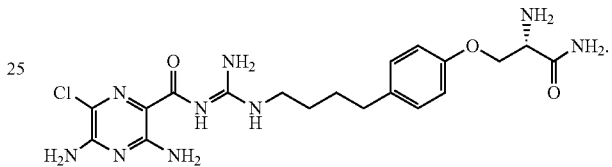

* * * * *